United States Patent [19]

Thompson et al.

[11] 4,301,804
[45] Nov. 24, 1981

[54] PACEMAKER WITH HALL EFFECT EXTERNALLY CONTROLLED SWITCH

[75] Inventors: David L. Thompson, Fridley; Stephen R. Duggan, Rosemount; Glenn M. Roline, Anoka, all of Minn.

[73] Assignee: Medtronic, Inc., Minneapolis, Minn.

[21] Appl. No.: 98,168

[22] Filed: Nov. 28, 1979

[51] Int. Cl.³ .............................................. A61N 1/36
[52] U.S. Cl. ................................................. 128/419 PG
[58] Field of Search ................................. 128/419 PG

[56] References Cited

U.S. PATENT DOCUMENTS 3,311,111  3/1967  Bowers ........................ 128/419 PG
4,126,139  11/1978 Walters et al. ............... 128/419 PG

FOREIGN PATENT DOCUMENTS 985797  3/1965  United Kingdom ......... 128/419 PG

Primary Examiner—William E. Kamm
Attorney, Agent, or Firm—Carl A. Forest; Lew Schwartz; Joseph F. Breimayer

[57] ABSTRACT

A body implantable cardiac pacemaker having a Hall effect switch which may be activated by a magnetic field in order to alter one or more pacemaker characteristics. A circuit in the pacemaker produces a strobe signal which is used to turn on a current flow through the Hall effect element once each pacemaker pulse cycle for a period of 25μ sec. The Hall effect element is part of an integrated circuit and is oriented in a plane parallel to the broad plane of the pacemaker.

8 Claims, 10 Drawing Figures

PACEMAKER WITH HALL EFFECT EXTERNALLY CONTROLLED SWITCH

BACKGROUND OF THE INVENTION

The invention in general relates to body tissue stimulators, and more particularly to a cardiac pacemaker having one or more characteristics that can be varied by means of a magnetically actuated switch.

The art of implantable cardiac pacemakers was first disclosed by Greatbatch in U.S. Pat. No. 3,057,356 entitled "Medical Cardiac Pacemaker", which issued in 1962. The device disclosed by Greatbatch included a relaxation oscillator that generated electrical pulses at a fixed rate. These pulses were applied to the heart through a lead to cause the heart to contract each time a pulse occured.

Early in the development of the art of cardiac pacemakers it became evident that it was desirable to design pacemakers so that the parameters of the output pulse could be varied. An early means for varying the output pulse incorporated a reed switch. See, for example, U.S. Pat. No. 3,311,111 issued to D. L. Bowers and U.S. Pat. No. 3,518,997 issued to R. W. Sessions. The reed switch is a pair of magnetically susceptible and conductive reeds which maintain themselves separated by spring action unless they are merged together by magnetic forces. Generally the magnetic forces are applied by means of a magnet held external to the body in which the pacemaker is implanted. Generally the closing of the reed switch by the magnet actuates circuitry within the pacemaker which alters the output parameters according to some predetermined scheme. By this means the output parameters of an implanted pacemaker can be adjusted externally of the body.

Many different schemes which incorporate a reed switch have been developed for adjusting the output parameters of an implanted pacemaker externally to the body. See for example U.S. Pat. Nos. 3,623,486 issued to Barouh V. Berkovits; 3,631,860 issued to Michael Lopin; 3,738,369 issued to Theodore P. Adams and David L. Bowers; 3,805,796 issued to Reese S. Terry Jr. and Gomer L. Davies; and 4,066,086 issued to Clifton A. Alferness and John M. Adams. The latter patent describes the method most commonly used, in which the reed switch is employed to actuate a circuit for receiving radio frequency programming signals. In this manner a wide variety of output parameters can be varied using a single switch. Because of the above developments, physicians have become accustomed to using magnets to vary output parameters of cardiac pacemakers.

Although the reed switch has become almost universal in pacemakers it is recognized as having several disadvantages. The reed switch is generally the only mechanical element in the pacemaker and for this reason it is more susceptible to damage and breakage than the electronic elements which make up the rest of the pacemaker. In addition, in order to fit into a pacemaker, the switch must be made very small which adds to its fragility. Generally, the tiny reeds of the switch are encased in a glass capsule for protection, but the glass capsule itself is susceptible to being fractured.

The modern pacemaker is generally wafer shaped so that it may be placed underneath the skin of the body with a minimum bulge. A characteristic of the reed switch is that, in order for it to respond to a magnetic field, it must be placed along the thin axis of the pacemaker, or at least have a component of its length along this axis. Generally, pacemakers are now thinner than the length of a typical reed switch so that incorporating a reed switch within the pacemaker in an orientation in which it operates reliably has become increasingly difficult. One attempt to overcome the disadvantages of a reed switch has been described in U.S. Pat. No. 3,766,928 issued to Goldberg et al. This method incorporates a potentiometer which is affixed to a small diametrically magnetized disc magnet. A second magnet is rotated outside the body to cause the disc magnet to rotate and turn the potentiometer. This method itself has numerous disadvantages including the fact that it is also mechanical, and very small and thus prone to breakage. In addition, the manipulation of the second magnet in order to adjust the potentiometer is more difficult and complex than the manipulation of the magnet required to actuate a reed switch.

Another aspect of the prior art of the present invention is the technology of the Hall effect. The state of the art in this technology is described in "Magnetically Activated Monolithic Integrated Circuits For Analog And Digital Applications", by Robert A. Anaselmo and Michael H. Oppenheimer, technical publication 71-11 published by the Sprague Electric Company and available from Technical Literature Service, Sprague Electric Company, North Adams, Mass. 01247. Although magnetically activated monolithic integrated circuits have been commercially available for about ten years they have not, up to now, been incorporated into pacemaker technology. There are numerous reasons for this. Pacemakers necessarily must be small and in addition implanted pacemakers necessarily have a limited supply of electrical energy so the current source must be totally contained in the pacemaker. However, magnetically activated Hall devices, whether in monolithic integrated circuit form or in other form, require complex supporting circuitry and draw large currents. Thus, Hall effect technology has generally been rejected for pacemaker purposes with the result that this technology is relatively unknown among those practiced in the pacemaker art.

SUMMARY OF THE INVENTION

It is an object of this invention to provide a cardiac pacemaker of the type having magnetically actuated output parameter altering means that overcomes one or more of the disadvantages discussed above.

It is another object of this invention to achieve the preceding object in a cardiac pacemaker that includes a solid state switch that may be activated by a magnetic field.

It is another object of this invention to achieve one or more of the preceding objects in a cardiac pacemaker that includes a circuit which utilizes the Hall effect.

It is a further object of the invention to achieve one or more of the preceding objects in a cardiac pacemaker in which a Hall effect switch is activated by a signal of duration less than 200 microseconds.

It is a further object of this invention to achieve one or more of the preceding objects in a cardiac pacemaker in which a strobe pulse is employed to cause current to flow in a Hall effect element.

It is another object of the invention to achieve one or more of the preceding objects in a cardiac pacemaker in which the circuit utilizing the Hall effect element draws little current.

It is another object of this invention to achieve one or more of the preceding objects in a cardiac pacemaker having a magnetically activated switch which is relatively durable.

It is another object of this invention to achieve one or more of the preceding objects in a cardiac pacemaker having a switch responsive to a magnetic field which is significantly smaller than a reed switch.

It is a further object of this invention to achieve one or more of the preceding objects in a cardiac pacemaker having a magnetically activated switch that operates effectively when oriented in a direction substantially parallel to the longer plane of the pacemaker.

It is yet another object of this invention to achieve one or more of the preceding objects in a pacemaker that incorporates no mechanical parts.

The invention comprises a body implantable pulse generator for providing stimulating pulses to living tissue, which pulse generator includes a Hall effect element capable of being activated by a magnetic field. Preferably the pulse generator also includes a means for causing electric current to flow through the Hall effect element for time periods that are shorter than the intervals between the time periods. Preferably the intervals are substantially equal to the intervals between the stimulating pulses provided by the pulse generator and the time periods when current flows through the Hall effect element are less than 200 $\mu$sec.

Numerous other features, objects and advantages of the invention will now become apparent from the following detailed description when read in conjunction with the accompanying drawings, in which:

DESCRIPTION OF THE PREFERRED EMBODIMENT

Figure 4:
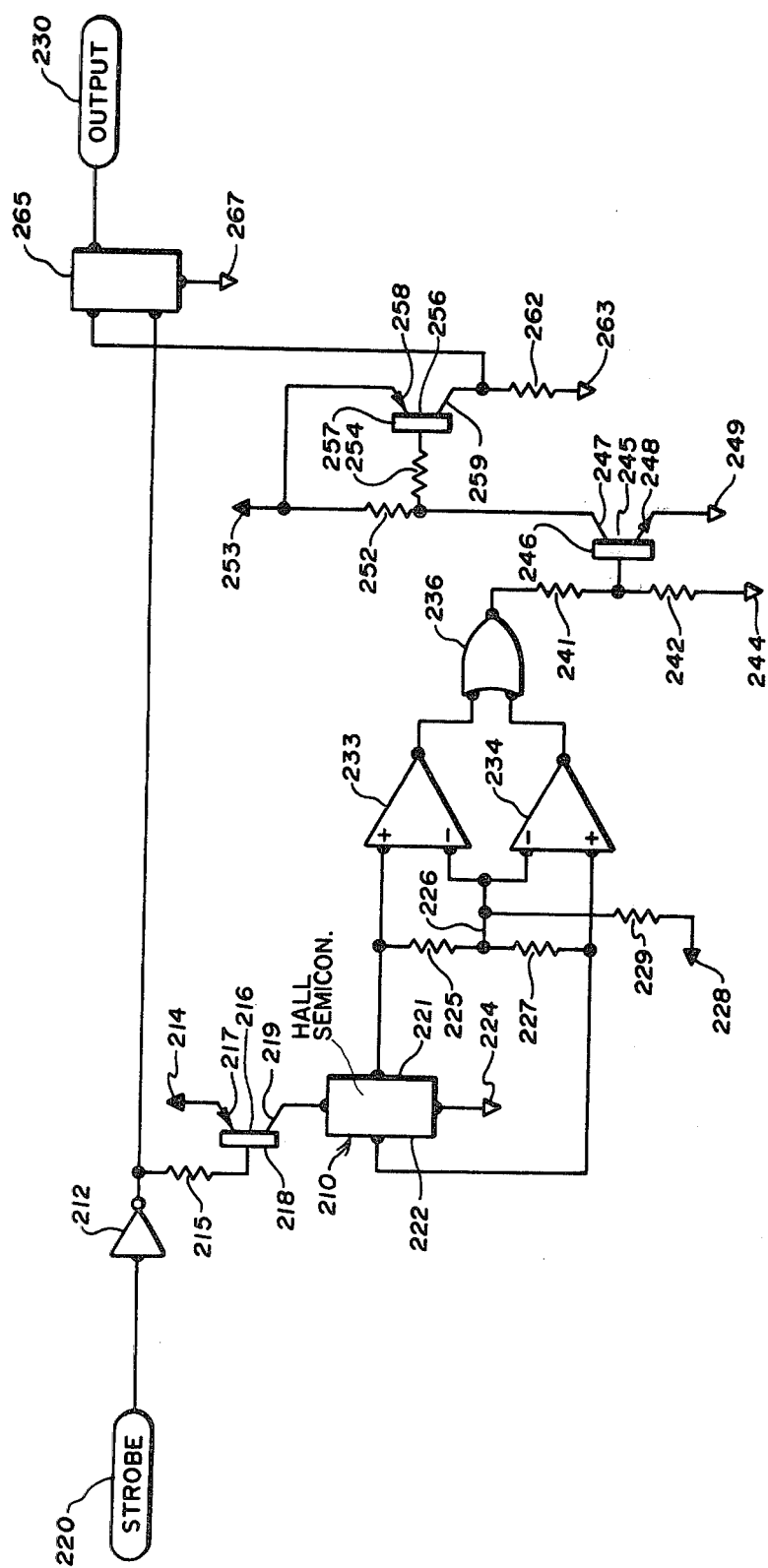
FIG. 4 shows the Hall effect circuitry.

Referring now to FIG. 4 of the drawings, the circuitry for incorporating the Hall effect magnetic switch into a pacemaker is shown. The Hall effect element at 210 is preferably oriented on an integrated circuit chip within the pacemaker so that the plane of the switch (corresponding to the plane of the paper of the drawing) lies in the same direction as the broad plane of the pacemaker. A strobe pulse from the pacemaker circuitry is input at 220 and activates Hall element 210 for a short period at periodic intervals, preferably once each pacemaker pulse cycle. If the pacemaker has been placed in an auxiliary magnetic field in the conventional manner (see for example U.S. Pat. No. 3,311,111 issued to D. L. Bowers) a positive voltage is output to the pacemaker circuitry at 230. This signal may be utilized within the pacemaker circuitry in a manner in which the signal generated by the closing of the conventional reed switch signal is utilized in the pacemaker; examples of apparatus and methods for utilization of the signal are discussed below, but these are not intended to be limiting.

In addition to the Hall effect element 210 the circuitry of FIG. 4 includes an inverter 212; resistors 215, 225, 227, 241, 244, 252 and 262; transistors 216, 245, and 256; operational amplifiers 233 and 234; an OR gate 236; and a d-type latch 265 (commonly referred to as a flip-flop). Connections to the positive voltage of the circuitry (also called the high or logic "1" voltage state) are shown by a solid triangle such as at 214. Connections to the ground state (also called the low or logic "0" state) of the circuitry are shown by open triangles such as at 224. Other than element 210, the circuit elements of FIG. 4 are all conventional and thus will not be described further.

The strobe pulse input at 220 is provided by the pacemaker circuitry which shall be described below. Strobe input 220 is applied to the input of inverter 212. The output of inverter 212 is applied to the clock input of latch 265 and to the base 218 of p-type transistor 216 through 20K resistor 115. The emitter 217 of transistor 216 is connected to the positive voltage source at 214, while its collector 219 is applied to one end of solid state switch element 210. The other end of the switch element 210 is connected to ground at 234. The sides of the switch element, which correspond to the switch terminals are connected to operational amplifiers 233 and 234. As shown in the drawing the left side is connected to the noninverting input of operational amplifier 234 while the right side is connected to the noninverting input of operational amplifier 233, although the choice of which side of the element 210 is connected to which of the operational amplifiers 233 and 234 is arbitrary. The inverting inputs of operational amplifiers 233 and 234 are connected to the positive voltage source at 228 through 22 megohm resistor 229. The inverting and noninverting inputs of operational amplifier 233 are connected through 2K resistor 225, and the noninverting inputs of operational amplifier 234 are connected through 10K resistor 227. The outputs of operational amplifiers 233 and 234 are applied as inputs to OR gate 236. The output of OR gate 236 is applied to the base of n-type transistor 245 through 10 K resistor 241. The base 246 of transistor 245 is also connected to ground 244 through 10 K resistor 242. The emitter of transistor 245 is connected to ground at 249 while the collector is connected to the positive voltage source at 253 through 10K resistor 252 and to the base of p-type transistor 256 through 10 K resistor 254. The emitter of transistor 256 is connected to the positive voltage source 253, while the collector 259 is connected to the data input of flip-flop 265 and to ground 263 through 100K resistor 262. The set and reset input of flip-flop 265 are connected to ground at 267. The "Q" output of flip-flop 265 is applied to output 230 to the pacemaker circuitry.

Solid state switch element 210 in the preferred embodiment is simply a piece of n-type silicon deposited on a ceramic chip along with other parts of the integrated circuitry of the pacemaker. Preferably the piece of silicon is approximately 30-40 mills square. If desired, a prefabricated Hall effect sensor element may be used, such as Microswitch No. 632SS4 manufactured by Honeywell, Inc. of Freeport, Ill. 61032.

The circuit just described operates in the following manner. The strobe pulse entering at 220 is generally a positive or a logic "1" signal of very short duration; in the preferred embodiment it is approximately 25 microseconds. The output of inverter 212 will thus be an approximately 25 microsecond negative pulse, which turns transistor 216 on causing a current to flow from voltage source 214 to ground 224 across switch element 210. The purpose of transistor 216 is to produce the appropriate current gain for driving the switch element 210. In the preferred embodiment the strobe output is rated at about 50 microamps whereas the solid state switch element 210 takes typically 5 to 10 milliamps, thus a current gain of 100 to 200 is required. Resistor 215 protects the emitter-base junction in a conventional manner.

If the Hall effect element 210 is in an auxiliary magnetic field when the 25 μsec pulse of current flows across it, then a voltage proportional to the magnetic field is produced at right angles to the direction of the current and the direction of the magnetic field. The voltage will be in the horizontal plane of the drawing if the magnetic field is into or out of the plane of the drawing, that is whether the north or south pole of the magnet is held above the pacemaker. As will be discussed below, the embodiment of the circuits shown respond properly whether a voltage from right to left, or from left to right is developed. It is contemplated that in some form of the invention a distinction may be made between the sign of the voltage, or what amounts to the same thing, between whether a north pole or a south pole magnet is held above the pacemaker. That is, if one pole is used which develops one sign of a voltage the pulse signal may be employed to produce a first effect in the pacemaker, while if the opposite magnetic pole is used and the opposite sign developed a second effect may be produced in the pacemaker.

Operational amplifiers 233 and 234 and resistors 225, 227 and 229 are set up to operate as a pair of comparators. The middle line 226 to the inverting input of operational amplifiers 233 and 234 provides a reference voltage. If the magnetic field applied to element 210 is such that the right side of the element goes high, operational amplifier 233 turns on and the output goes to a high or logic "1" state; on the other hand, if the left side 222 of element 210 goes high then operational amplifier 234 turns on and its output goes to a logic "1". Thus, if element 210 is in the auxiliary magnetic field there will be a logic "1" signal on one of the inputs to OR gate 236 and therefore its output will become a logic "1".

The purpose of the circuit containing transistors 245 and 256 is to provide current gain and at the same time to invert the signal from OR gate 236 twice so that it will have a proper sign to produce the correct output at flip-flop 265. The logic "1" signal of OR gate 236 turns n-type transistor 245 on which puts a low or logic "0" signal on the base of p-type transistor 256, which in turn, turns that transistor on, and places a positive or logic "1" signal on the d input of flip-flop 265. This circuit may be eliminated in some embodiments of the invention. For example, if the Hall circuitry is implemented with CMOS type logic in an integrated circuit then the output of OR gate 236 will have a sufficient power level to trigger gate 265 without the need for power gain. Thus, in this case, the output of OR gate 236 may be applied directly to the data input of gate 265 and the invention will operate as described below.

If element 210 is in a magnetic field, the rise and fall of the signal on the d input of flip-flop 265 will follow the rise and fall of the strobe pulse with a slight delay. The delay is due to the time constant of the circuitry described above; that is, it takes a finite amount of time for each of the circuit elements such as operational amplifiers 233 and 234 and transistors 216, 245, and 256 to respond to signals at their inputs. Thus, when the inverter strobe signal from the output of inverter 212 is going from logic "0" to a logic "1" (the tail of the strobe pulse) the data input of flip-flop 265 will still be at a logic "1", and will remain so for the period of the delay through the circuit. The change of the pulse applied to the clock input of flip-flop 265 from logic "0" to logic "1" clocks the "Q" output of flip-flop 265 to the value of the data input, which is a logic "1". Since the set and reset inputs are held at logic "0" the "0" output of flip-flop 265 remains at a logic "1" until the flip-flop is clocked while a logic "0" signal is applied to its data input. From the discussion above it is seen that this will happen on the first strobe pulse after the magnetic field is removed from the pacemaker and thus from element 210. Thus, the net effect of the invention is to provide a high or logic "1" signal at the output 230 substantially during the time period between the first strobe pulse after the magnetic field is placed output 230 substantially during the time period between the first strobe pulse after the magnetic field is placed on the pacemaker until the first strobe pulse after the magnetic field is removed from the pacemaker.

The strobe signal is a feature of the invention. An important characteristic of the strobe signal is that the period of time in which the signal is "ON" is shorter than the intervals between signals. As discussed above, in the embodiment of the invention described, the strobe signal lasts for a period of 25 μsec and as will be described below the intervals between the strobe signals are of the order of ½ to 1 second. Preferably, the time period in which the strobe is on is less than 200 sec; however, any period which is shorter than the time intervals between the strobe signals is within the contemplation of the invention.

In the circuit of the invention the solid state switch element 210 has about 250 nanoamps of average current drain. This current drain is very small compared to the total current drain of a conventional pacemaker, and thus the incorporation of the solid state magnetic switch circuit of the invention into the pacemaker does not substantially decrease the longevity of the pacemaker.

Figure 1:
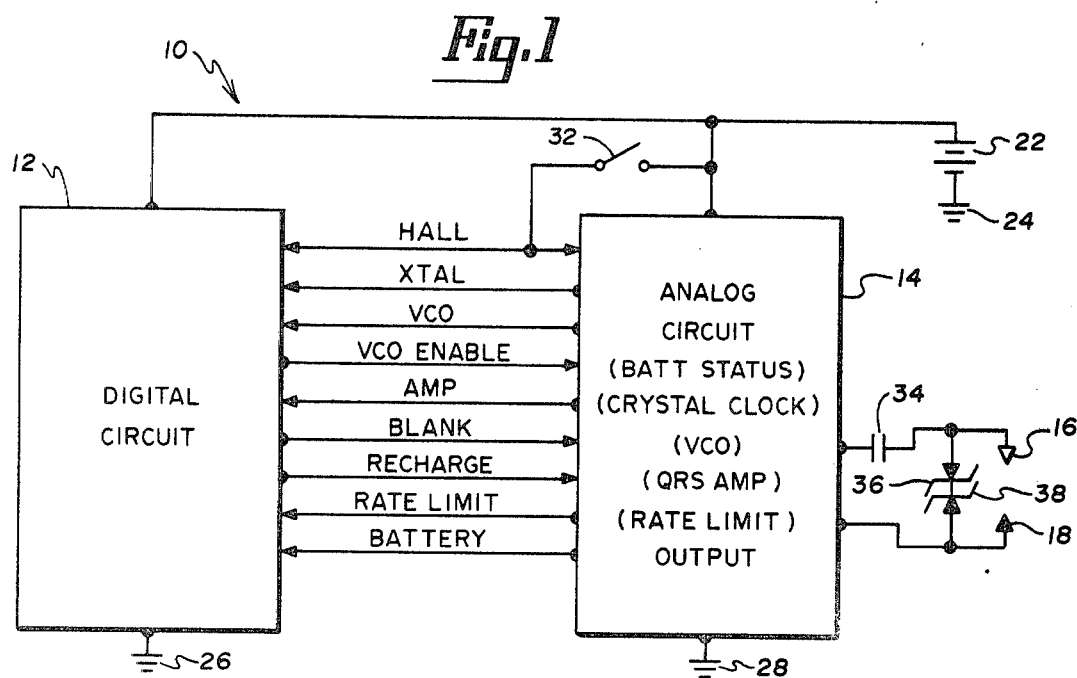
FIG. 1 is a block schematic diagram of the pacemaker circuitry for a preferred embodiment of the invention showing the various signals provided between the digital and analog portions of the circuit.

Turning now to the description of the pacemaker circuitry which produces the strobe pulse, FIG. 1 shows a schematic diagram of a cardiac pacemaker circuit according to an exemplary embodiment of the invention. The cardiac pacemaker 10 includes a digital circuit 12 which communicates with an

| |
|---|
| X |
| X |
| X |
| X |
| X |
| X | analog circuit 14 to produce an electrical pulse which is delivered via outputs 16 and 18 to leads (not shown) for application to the heart (not shown) to cause the heart to contract. The leads through which the pulses are applied to the heart, the type of pulses applied, and the response of the heart to the pulses is well known in the art and will not be discussed herein.

The embodiment of the pulse generator 10 which shall be described is of the type that is implantable within the human body. However, nothing herein should be construed as limiting the invention described solely to the implantable type pulse generators.

The analog circuit as shown in FIG. 1 consists of a number of generally separate electrical systems. These systems include a battery status monitor, a crystal oscillator clock, a voltage control oscillator clock, a QRS sensing amplifier, a pulse rate limiting circuit and output circuitry which includes a voltage doubler. Each of these analog systems are well known in the art and will not be discussed in detail herein. For a complete description of certain of these circuits reference is made to the following patent applications, commonly owned with the present application: Ser. No. 957,812, entitled "Demand Cardiac Pacemaker Having Reduced Polarity Disparity" invented by Jerome T. Hartlaub and Ray S. McDonald, and Ser. No. 957,828 entitled "Cardiac Pacemaker Having Rate Limit" invented by David L. Thompson and Ray S. McDonald.

The digital circuit 12 includes the mode selection circuitry, the digital logic necessary to produce each of the selectable output modes, and digital timing means for causing pulses to be generated from pulse generator 10 in the selected manner. A more detailed description of digital circuit 12 is given below in the discussion relating to FIGS. 2a and 2b and a still more detailed description is given in the discussion with respect to FIGS. 3a, 3b, 3c, 3d, 4 and 5.

Both the digital and analog circuits are powered by battery 22, which may be a conventional lithium-iodide battery generating +V, or approximately 2.8 volts, connected between a source of reference potential, such as ground 24, and the circuits 12 and 14. In the present description a signal at the power supply voltage may be referred to alternatively as a logic "1" or a high signal. A signal at the ground voltage may be referred to alternatively as a logic "0" or a low signal. The digital circuit 12 is connected to ground at 26 and the analog circuit 14 is connected to ground at 28. Switch 32 is the Hall effect switch described above with reference to FIG. 4 and may be "closed" by placing a magnet (not shown) in close proximity to pulse generator 10 in a manner well known in the art. When HALL EFFECT switch 32 is "closed" a +V volts or a logic "1" HALL signal is applied both to digital circuit 12 and analog circuit 14. When the magnet is removed from the vicinity of the pulse generator 10 HALL switch 32 "opens" and a ground, or logic "0" signal is applied to digital circuit 12 and analog circuit 14. The manner in which such signals are applied shall be described in more detail below.

As mentioned above, outputs 16 and 18 communicate with conventional cardiac pacemaker leads to apply the pulse generator signal to the heart. Output 18 may consist of the outer metal casing of pulse generator 10 or it may connect with an electrode wire within a lead system, depending upon the type of cardiac pacemaker lead selected. Output 16 is coupled to analog circuit 14 through a capacitor 34 to prevent DC leakage in the case of some system failures. A pair of diodes 36 and 38 have their anodes coupled together and their cathodes coupled to outputs 16 and 18 respectively. Diodes 36 and 38 function in the conventional manner to prevent damage to the circuitry of pulse generator 10 in the case of large extraneous signals, such as may be caused by electrocautery.

Analog circuit 14 provides the XTAL, VCO, AMP, RATE LIMIT and BATTERY signals to digital circuit 12. Digital circuit 12 provides the VCO ENABLE, BLANK, and RECHARGE signals to analog circuit 14.

The XTAL signal is a square-wave pulse signal occurring at a frequency of 32,768 Hz and the VCO is a square-wave pulse signal having a frequency of 20,000 Hz whenever the voltage of battery 22 is equal to 2.8 volts and decreases approximately proportional to the square of the voltage to about 10,000 Hz when the battery voltage is equal to 2.0 volts. This decrease of the VCO frequency is used, as shall be explained in more detail below, to provide an increase in the pulse width as the voltage from battery 22 decreases, in order to maintain a constant energy of the pulse.

The VCO ENABLE signal provided from digital circuit 12 to analog circuit 14 is normally a logic "1". However, at the time the stimulation pulse is to be provided, the VCO ENABLE signal becomes a logic "0" and the VCO is enabled to begin providing pulses. The VCO ENABLE signal remains logic "0" until after the stimulating pulse has been provided, at which time it returns to logic "1" and the VCO becomes disabled.

The AMP signal is provided from the output of the analog QRS sensing amplifier and is normally a logic "1" signal. Each time the QRS amplifier senses a naturally occurring QRS signal, it becomes a logic "0" pulse signal.

The BLANK signal provided from digital circuit 12 is normally a logic "1" which becomes logic "0" for approximately 100 msec following the provision of a stimulating pulse from pulse generator 10 or the sensing of a natural heartbeat. The BLANK signal is used to prevent the QRS sensing amplifier within analog circuit 14 from sensing any signals during the 100 msec time interval and to allow the components within the sensing amplifier circuit to reset themselves after sensing a signal.

The RECHARGE signal is a normally logic "0" which becomes logic "1" for approximately 10 msec after the stimulating pulse has been provided by generator 10. The purpose of the RECHARGE signal is to close a switch in analog circuit 10 to allow an output capacitor to recharge after every output pulse.

The RATE LIMIT signal which is provided from analog circuit 14 to digital circuit 12 is a normally logic "0" signal which becomes logic "1" after the provision of the stimulation pulse for approximately 500 msec to set an upper rate limit of approximately 120 pulses per minute for pulse generator 10. This rate limitation function is used as a backup and safety feature against the possibility of an integrated circuit or crystal oscillator failure that may cause high rate output to occur.

The BATTERY signal applied from analog circuit 14 to digital circuit 12 is a logic "1" signal so long as the voltage provided from battery 22 is above a certain minimum level, for example 2.0 volts, and is a logic "0" signal whenever the voltage from battery 22 falls below the minimum level.

Figure 2:
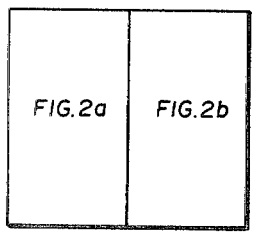
FIG. 2 shows the arrangement of FIGS. 2a and 2b which in turn show, in block format the digital circuitry portion of the invention.
Figure 2A:
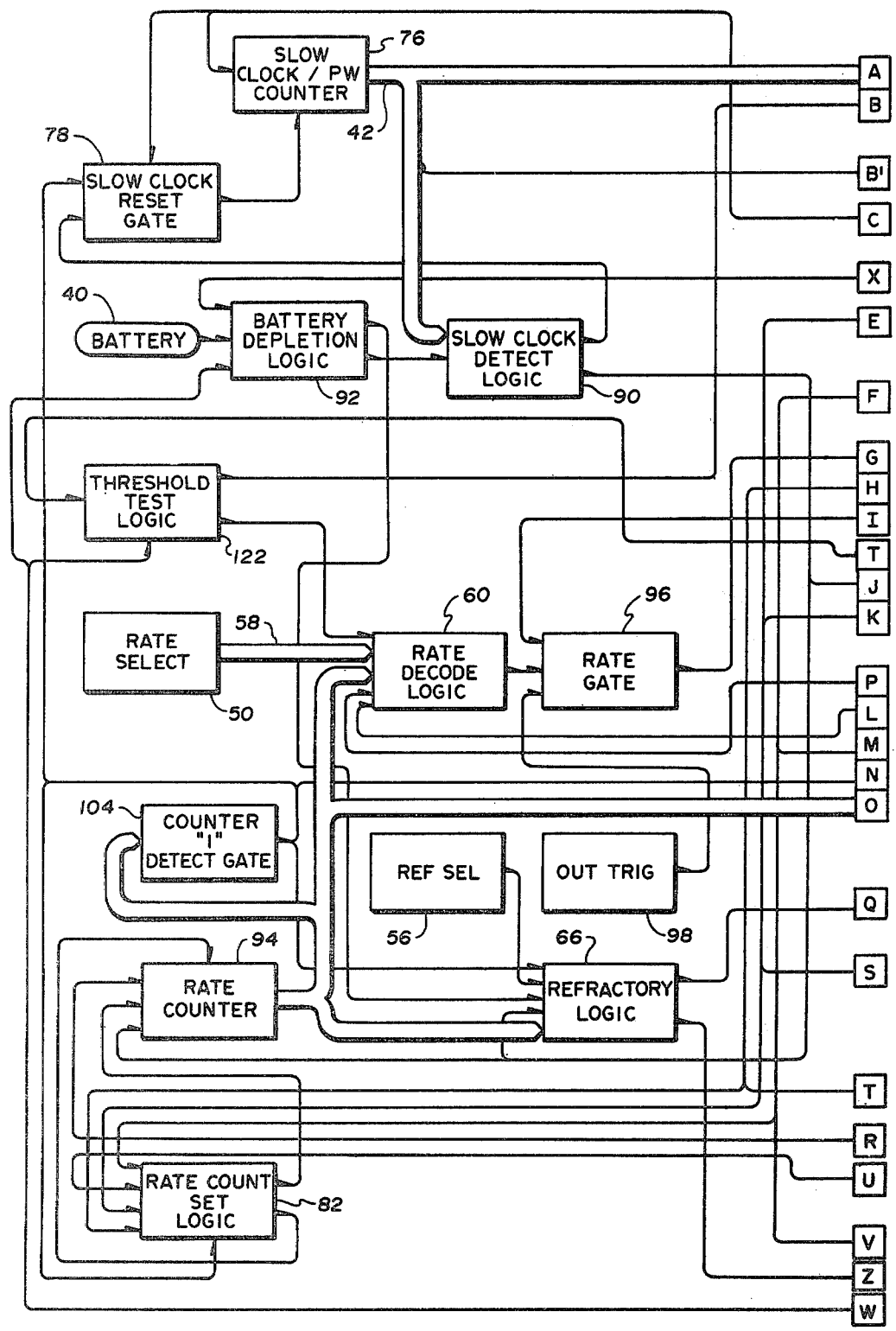
Figure 2B:
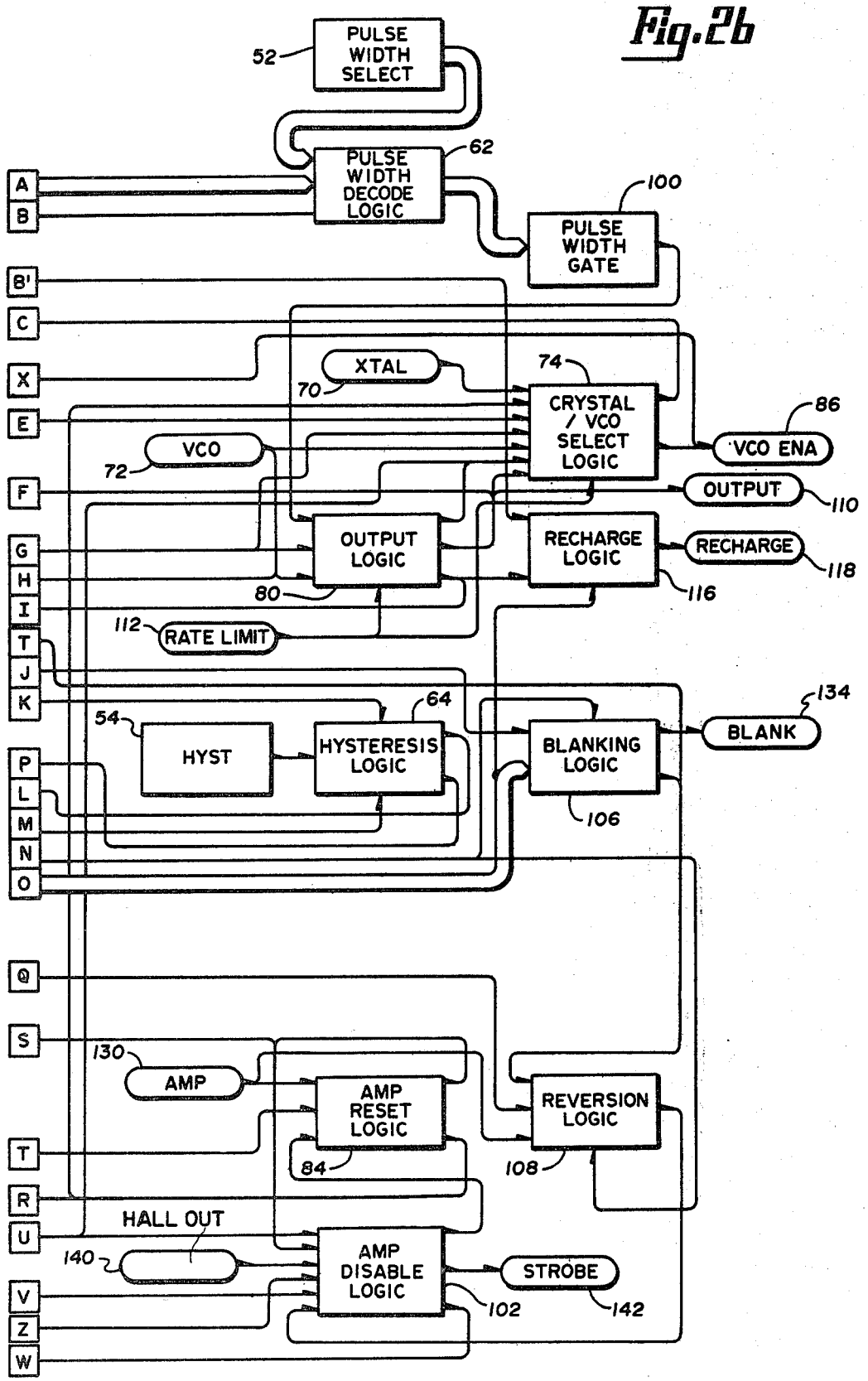

Referring now to FIG. 2, there is shown the manner of arranging FIGS. 2a and 2b to form a block diagram of digital circuit 12. In FIGS. 2a and 2b any signals which are received from, or applied to analog circuit 14 are designated by the particular label for the signal placed within an oval, for example the battery signal just discussed above is shown at 40 in FIG. 2a. The oval labeled "strobe" is an output to the strobe input 220 in FIG. 4 and to other portions of the digital circuit which shall be described below. All provisions of power supply voltage or ground coupled to each block have been deleted, although it should be understood that these signals are necessary and should be coupled in a known and accepted manner of designing digital logic circuits. For each of the blocks shown in FIGS. 2a and 2b data signals are shown as being applied to the left side of the block, reset signals are shown as being applied to the bottom of the block, set signals are shown as being applied to the top of the block, and output signals are shown as originating from the right side of the block. Arrows pointing into the block indicate a signal applied to the block, whereas arrows pointing out of the block designate a signal originating from the block. Wherever a plurality of lines are transmitted from, or to a particular block circuit, such as a parallel output from a counter or shift register such plurality of lines are represented as wide lines such as at 42 in FIG. 2a.

Turning now to a description of the manner in which the various subcircuits of the pacemaker are connected and interact as shown in FIGS. 2a and 2b, the pulse rate and hysteresis rate selection circuitry is shown at 50, the pulse width selection circuitry is shown at 52, the hysteresis function selection circuit is shown at 54, and the refractory period selection circuit is shown at 56. Eleven pulse rates and two hysteresis rates are selectable. Selecting a rate, as shall be described below, causes a predetermined combination of logic "1" and logic "0" signals to be output from rate selection circuitry 50 and applied to rate decode logic circuitry 60. If the hysteresis function is selected a logic "0" signal is output from hysteresis function selection circuitry 54 and applied to hysteresis logic 64; if the nonhysteresis function is selected a logic "1" signal is output and applied between the same circuits. The selection of the pulse width causes a predetermined set of logic "0" and logic "1" signals to be output from the pulse width selection circuitry 52 and applied to the pulse width decode logic circuitry 62. Selection of the refractory period causes a predetermined one of either a logic "0" or a logic "1" signal to be output from refractory selection circuitry 56 and applied to refractory logic 66.

The timing of the pulse generator function is provided by the XTAL oscillator and VCO oscillator signal originating from analog circuit outputs 70 and 72 respectively, and having the frequencies described above. The XTAL and VCO outputs 70 and 72 are applied to crystal/VCO select logic 74. The VCO output also communicates directly with output logic 80, rate count set logic 82, and amp reset logic 84. Crystal/VCO select logic 74 selects one of the XTAL or VCO signals and provides it as the upper output signal which is applied to slow clock/PW counter 76 and to the set input of the slow clock reset gate 78. If any of the inputs to crystal/VCO select logic 74 (other than the XTAL and VCO inputs) are a logic "1" the circuitry selects the VCO signal, and at the same time applies a logic "0" signal through its lower output to VCO ENABLE output 86. If all of the inputs (other than the XTAL and VCO inputs) are a logic "0" the XTAL signal is selected and a logic "1" signal is output to VCO ENABLE 86. If the upper output of the crystal/VCO select logic, either XTAL or VCO provides a fast clock signal for the pulse generator circuit. The VCO pulse starts low (logic "0") and is triggered by the XTAL clock pulse with the result that there is an apparent synchronization between the XTAL and VCO clocks.

Slow clock/PW counter 76 is an eightstage binary counter connected in a known manner. The output signal from slow clock 76 is provided to slow clock detect logic 90, to recharge logic 116 and to pulse width decode logic 62. When slow clock/PW counter 76 counts 179 fast clock cycles detect logic 90 reads this count and provides an output signal through its upper output to slow clock reset gate 78, which in turn provides an output signal to reset slowclock/PW counter 76. The resetting of the slow clock/PW counter 76 after each 179 fast clock cycles determine a time interval called slow clock which is equal to approximately 5.49 msec.

Slow clock detect logic 90 provides a slow clock signal through its lower output to rate counter 94, which is an eightstage binary counter connected in a known manner. The output of rate counter 94 is provided to rate decode logic 60, counter "1" detect gate 104, refractory logic 66, blanking logic 106, and recharge logic 116. The count of rate counter 94 is read by rate decode logic 60 and when the number of counts determined by the inputs to rate decode logic from rate select 50 and hysteresis logic 64 is reached, rate decode logic 60 provides an output signal to rate gate 96. The output from rate gate 96 is provided to crystal/VCO select logic 74, in order to turn on the VCO oscillator as described above, and to output logic 80 in order to initiate the pulse output sequence as shall be described below. Output trigger 98 is a test pin by means of which an external output can be applied to rate gate 96 to force the pulse generator into rate limit either to test the rate limit circuitry and/or in order to perform a laser trim of a resistor on the rate limit circuitry at the time of manufacture.

Output logic 80 is responsive to signals from the upper output of crystal/VCO select logic 74, and the outputs of rate gate 96 and VCO output 72. The reset input of output logic 80 is responsive to the rate limit output 112 from analog circuit 14. The upper output of output logic 80 is applied to crystal/VCO select logic 74, to rate count set logic 82 and to amp disable logic 102. The middle output is applied to crystal/VCO select logic 74, to output 110 to the analog circuit, to rate count set logic 82, to amp disable logic 102 and to the reset input of hysteresis logic 64. The lower output is applied to recharge logic 116 and rate gate 96.

As mentioned above the signal from rate gate 96 activates the VCO oscillator. On the first VCO pulse output logic 80 is clocked and its upper output changes from logic "0" to logic "1". This signal is applied to crystal/VCO select logic 74 to shut off the VCO oscillator during the period in which the pacemaker is in rate limit as shall be discussed further below, and clocks rate count set logic 82 so that its lower output goes to logic "1". This signal is applied to the set input of rate counter 94 to force all its stages to a logic "1" output state. Counter "1" detect gate 104 detects this "all 1's" condition and changes its output from logic "0" to a logic "1". This signal from counter "1" detect gate is applied to slow clock reset gate 78 to reset slow clock/PW counter 76 and to the reset input of rate count set logic 82.

On the next VCO oscillation output logic 80 is again clocked and its middle output changes from logic "0" to logic "1". The application of this signal to output 110 initiates the pulse generator output in analog circuit 14. The same signal applied to crystal/VCO select logic 74 continues to enable the VCO oscillator for the duration of the output pulse. The signal is also applied to rate count set logic 82 to enable it so that on the next VCO oscillation its upper output goes from logic "0" to logic "1". This signal is in turn applied to rate counter 94 and clocks it to an overflow condition removing the logic "1" status of each of its stages to prepare the rate counter for the next count cycle.

Rate limit output 112 from analog circuit 14 is applied to the reset input of output logic 80 and to crystal/VCO select logic 74. The rate limit function is a secondary one-shot function on a separate die and is used as a backup against the possibility of integrated circuit or crystal oscillator failure which might create high rate output. The signal applied from rate limit output 112 is normally a logic "0", but during an approximately 500 msec period following the output pulse it is a logic "1". The logic "1" signal applied to the reset input of output logic 80 holds the middle output at a logic "0" until the end of the rate limit period, thereby blocking the output pulse during this period. Thus the rate limit output inhibits rates faster than approximately 120 beats per minute and does not allow the output to go to a 2:1, 3:1, etc. divide condition. The circuitry of output logic 80 is such that if an output pulse were to be called for before the rate limit time period had elapsed, the circuitry is held reset. Then, on the next positive clock transition after the rate limit interval runs out and the signal from rate limit 112 returns to logic "0" the output pulse is initiated.

The signal from rate limit 112 applied to crystal/VCO select logic 74 shuts off the VCO oscillator during the period in which the upper output logic 80 is logic "1" and the rate limit circuitry is on. Thus, if the pacemaker is in a runaway condition in which the output pulse is being called for during the rate limit period, the VCO oscillator is held in the OFF condition. This function minimizes current drain if a runaway condition should arise.

As discussed above, just prior to the initiation of the output pulse the rate counter is set to an "all 1's" condition which condition is detected by counter "1" detect gate 104 which thereupon signals slow clock reset gate 78 to reset slow clock/PW counter 76. Slow clock/PW counter 70 then begins increasing its count again in response to VCO oscillator pulses from crystal/VCO select 74. Pulse width decode logic 62 reads the count of slow clock/PW counter 76, and when it has reached a count determined by the output of pulse width select 52, pulse width decode logic 62 provides a signal to pulse width gate 100. The output of pulse width gate 100 is provided to output logic 80 to enable the output circuitry so that the output pulse is terminated on the next VCO clock cycle.

The lower output of output logic 80 changes from logic "0" to logic "1" at the termination of the output pulse. This signal is applied to the recharge circuitry to enable it so that after a period determined by a signal provided from slow clock/PW counter 76 the output from recharge logic 116 goes from logic "0" to logic "1" to initiate the recharge interval. This signal is applied to the analog circuit through recharge output 118. Approximately 10 msec after the initiation of the recharge interval recharge logic 116 is reset via a pulse from rate counter 94 and thereby resetting the output to logic "0" to terminate the recharge interval.

Battery output 40 from the analog circuit 14 is provided to battery depletion logic 92. Battery depletion logic 90 is also responsive to the lower output of amp disable logic 102 and the upper output of crystal/VCO select logic 74. The upper output of battery depletion logic 92 is provided to refractory logic 66 and the lower output is provided to slow clock detect logic 90. Battery depletion logic 92 is clocked by crystal/VCO select logic 74 each time the VCO is enabled just prior to an output pulse. This timing of the clock signal prevents supply ripple during or for a period after the pulse from prematurely triggering the battery depletion condition. If the battery is depleted, battery depletion logic 92 provides a logic "0" signal at its lower output which is applied to slow clock detect logic 90 to extend the slow clock interval by 11.1 percent to provide a 10 percent slowdown in the pulse rate. At the same time, a logic "1" signal is provided to refractory logic 66, from the lower output of battery depletion logic 92 to ensure a stable refractory interval as described below. The battery depletion logic circuit is latchable; i.e. if the battery signal shows depletion at the time of any clock pulse provided by crystal/VCO select logic 74, then any subsequent clock pulse results in the output which extends the slow clock interval. The logic may be "unlatched" by the signal from amp disable logic 102, which is provided whenever Hall effect switch 32 is closed. If the BATTERY signal no longer is indicating battery depletion at the time that the Hall effect switch is closed then the battery depletion logic resets to its normal output. However, if the BATTERY signal indicates battery depletion at the time that the Hall effect switch is closed then battery depletion logic 92 remains latched.

We now turn to a discussion of the pacemaker circuitry related to the demand function of the pulse generator, i.e. the function that prevents a generated pulse from being output if a natural heartbeat is detected. Amp output 130 from analog circuit 14 is provided as one input to amp reset logic 84. Other inputs to amp reset logic 84 are from VCO output 72 and the middle output of amp disable logic 102. The upper output of amp reset logic 84 is applied as an input to rate count set logic 82, amp disable logic 102, crystal/VCO select logic 74, and as the set input to hysteresis logic 64. The lower output is provided as an input to rate counter 94 and crystal/VCO select logic 74. In normal operation of the pacemaker a detected heartbeat causes a clock signal to be applied to amp reset logic 84 from output 130. If the middle output of amp disable logic 102 is a logic "1" the clock signal from output 130 causes the upper output of amp reset logic 84 to change to a logic "1" state. The logic "1" signal applied to rate count set logic 82 causes rate counter 94 to be set to "all 1's" as described above and the signal to crystal/VCO select logic 74 turns the VCO on. On the first VCO pulse amp reset logic 84 is clocked to provide a logic "1" signal at its second output which is applied to rate counter 94 and crystal/VCO select logic 74. The signal to the rate counter 94 clocks the rate count stages to an overflow condition, while the signal to crystal/VCO select logic 74 maintains the VCO ON condition. Amp reset logic 84 resets itself at the same time so that the upper output goes to a logic "0" and one VCO pulse later the second output goes to a logic "0" thereby turning off the VCO and readying the amp reset logic for the next cycle triggered by the next natural heartbeat.

Blanking logic 106 is responsive to the lower output of slow clock detect logic 90 and the output of rate counter 84. Its set input is responsive to the output of counter "1" detect gate 104. The upper output of blanking logic 106 is provided to blank output 134 and the lower output is provided to reversion logic 108 and threshold test logic 22. Blanking logic 106 is clocked each time the lower output of slow clock detect logic 90 changes from logic "0" to logic "1". Most of these clock pulses have no effect on the output states of blanking logic 106 because the circuitry has a self-latching loop that causes the output to retain their previous state with each clock pulse. This state is normally a logic "1" for the upper output and also a logic "1" for the lower output. The signal from counter "1" detect gate 104 however sets blanking logic 106 at the beginning of the output pulse and after a natural heartbeat is sensed. This changes the upper output to a logic "0" to initiate the blanking period and also changes the lower output to a logic "0". The SET signal from counter "1" detect gate 104 goes to a logic "0" on the next VCO pulse, however the blanking logic 106 maintains itself latched in the blanking output condition until approximately 100 msec after the initiation of the pulse when the signal from rate counter 94 relatches blanking logic 106 into the "non-blanking" state described above, thereby terminating the blanking interval. During the blanking interval the re-sensing amplifier in analog circuit 14 is blanked thereby preventing any input to amp reset logic 84 from amp output 130.

Amp disable logic 102 is responsive to the outputs of Hall Circuit input 140 and reversion logic 108, the lower output of refractory logic 66, the upper output of amp reset logic 84, and the middle and upper outputs of output logic 86. Hall circuit input 140 carries the signal from output 230 of FIG. 4. The lower output of amp disable logic 102 is provided to threshold test logic 122 and battery depletion logic 92. The middle output is provided to amp reset logic 84, while the upper output provides a strobe output 142 which is used elsewhere in the digital circuit and shall be described below. The output to strobe 142 is a logic "0" except in two instances: it is a logic "1" in the time period between the two output pulses from output logic 86, a time period of approximately 25 sec just at the initiation of the output pulse; it is also a logic "1" during the time in which the upper output from amp reset logic 84 is a logic "1", that is the period during which the rate counter is being set after each detected natural heartbeat, again a very short period. The lower output of amp disable logic 102 is normally a logic "1" but goes to a logic "0" during a time period between the trailing edge of the first strobe pulse after the Hall Effect switch 32 is closed until the trailing edge of the first strobe pulse after Hall Effect switch 32 is opened. The middle output of amp disable logic 102 is normally logic "1" whenever either the lower output from refractory logic 55 or the output from reversion logic 108 is a logic "0". The middle output is also a logic "0" during the period described above when the lower output is "0", that is during the approximate time period during which the Hall Effect switch is closed.

Refractory logic 55 is responsive to the output of refractory select 56, the upper output of battery depletion logic 92, the lower output of slow clock detect logic 90, and to the output of the rate counter 94. The set input of refractory logic 55 is responsive to the output of counter "1" detect gate 104. The upper output of refractory logic 66 is applied to reversion logic 108, while the lower output is applied to amp disable logic 102. The output of counter "1" detect gate 104 goes to logic "1" just prior to the initiation of the output pulse, and just after the detection of a natural heartbeat as described above. This logic "1" signal sets refractory logic 66 causing its upper output to go to logic "1" and its lower output to go to logic "0". As can be seen from a discussion of the amp disable logic 102 and amp reset logic 84 above the logic "0" state of the lower output of refractory logic 66 causes the middle output of amp disable logic to go to a logic "0" which in turn disables amp reset logic 84 from activation of rate count set logic 82. When the rate counter reaches the count which determines the refractory period the input to refractory logic 66 from rate counter 94 goes to a logic "1". The trailing edge of the same clock pulse from slow clock detect logic 90 that advanced rate counter 94 to the refractory count, clocks refractory logic 66 so that its upper output goes to a logic "0" while its lower output goes to a logic "1". This terminates the refractory period and allows the amp reset function to operate as discussed above. If the output of refractory select 56 is logic "0" a 325 msec refractory period is selected; if the output is a logic "1", a 400 msec refractory period is selected. As mentioned above, the input to refractory logic 66 from battery depletion logic 92 causes the refractory logic 66 to recognize an earlier count from rate counter 94 in order that the 11 percent slowdown of the slow clock and rate counter after the battery is depleted is offset and a stable refractory interval is obtained.

Reversion logic 108 is responsive to the lower output of blanking logic 106, the upper output of refractory logic 66, and the output of amp output 130. The output of counter "1" detect gate 104 is applied to the reset input of reversion logic 108. The output of reversion logic 108 is applied to amp disable logic 102 as discussed above. The logic "1" signal from counter "1" detect gate 104 resets reversion logic 108 just prior to the initiation of the output pulse or just after a natural heartbeat. The reset signal places a logic "1" signal on the reversion logic 108 output. At the same time the upper output of refractory logic 66 has become a logic "1" also. At the end of a 100 msec blanking interval the lower output of blanking logic 106 becomes a logic "1" as discussed above. With the inputs from both refractory logic and blanking logic being a logic "1" reversion logic 108 is enabled to receive inputs from amp output 130. This enabling period ends when the upper output of refractory logic 66 goes to a logic "0" at the end of the refractory interval. If two pulses from the amp output 130 are received during this reversion interval the output of reversion logic 108 goes to a logic "0" disabling the amp reset logic 84 through amp disable logic 102 as discussed above with respect to the refractory function. Since the refractory interval is either 325 or 400 msec the reversion interval is either 225 or 300 msec; therefore the fact that the reversion is effective if two pulses are detected means that any continuous signal of frequency greater than 8.8 Hz or 6.6 Hz (depending upon the refractory period chosen) is rejected by the reversion circuit.

Hysteresis logic 64 is responsive to the output of the hysteresis function select circuit 54, has a set input from the upper output of amp reset logic 84, and has a reset input from the middle output of output logic 86. Both the upper and lower outputs of hysteresis logic 64 are applied to rate decode logic 60. As discussed above, the amp output 130 signals a detected heartbeat the upper output of amp reset logic 84 goes to a logic "1". This signal sets hysteresis logic 64 so that the upper output goes to logic "1" while the lower output goes to a logic "0". The logic "1" signal is applied to rate decode logic 60 to enable the hysteresis rate. The logic "0" output is applied to rate decode logic 60 to disable all possible pacemaker rates except the two hysteresis rates. Hysteresis logic 64 will remain in this state as long as the heartbeat rate remains above the hysteresis rate, since each natural heartbeat resets rate counter 94 so that the hysteresis count is not reached. If the heartbeat drops below the hysteresis rate the counter reaches the hysteresis count and signals for an output pulse through rate gate 96 as described above. When the output pulse is initiated by the logic "1" signal from the middle output of output logic 86, a logic "1" reset signal is applied to hysteresis logic 64. The signal causes the upper output of hysteresis logic 64 to change the logic "0" state and the lower output to change to a logic "1" state. The logic "0" signal disables the hysteresis rate in rate decode logic 60 while the logic "1" signal enables the "normal" rates in rate decode logic 60 to provide an output signal at the selected rate. This continues until a natural heartbeat is again detected and the cycle repeats. If the output from hysteresis function select 54 is a logic "0" the upper output of hysteresis logic 64 will remain at a logic "0" state while the lower output will remain at a logic "1" state, which disables the hysteresis function. If the output of hysteresis function select 54 is a logic "1" the hysteresis function is enabled and hysteresis logic 64 operates as discussed.

Threshold test logic 122 is responsive to the lower output of blanking logic 105. The reset input of threshold test logic 122 is responsive to the lower output of amp disable logic 102. The upper output of threshold test logic 122 is applied to pulse width decode logic 62 while the lower output is applied to rate decode logic 60. As discussed above the lower output of amp disable logic 102 is normally a logic "1" which signal holds threshold test logic reset. Both outputs are held in the logic "0" state in this situation. The closing of the Hall effect switch 32 places a logic "0" signal on the lower output of amp disable logic 102 coinciding with the trailing edge of the strobe pulse which comes just at the initiation of the output pulse. This signal enables threshold test logic 122. There is no immediate effect on the rest of the pulse generator circuit. A normal output pulse or natural heartbeat (whichever is dictated by the circumstances) occurs. At the end of the 100 msec blanking period following either the normal output pulse or natural heartbeat the lower output of blanking logic 106 changes from a logic "0" to a logic "1". This signal clocks threshold test logic 122 which changes the lower output to a logic "1", while the upper output remains at a logic "0". The logic "1" signal is applied to rate decode logic 60 to enable the 100 pulse per minute rate. The next output pulse therefore occurs in 600 msec, unless the pacemaker rate or the natural heartbeat rate is faster than 100 beats per minute, in which case a pulse or natural heartbeat at this faster rate occurs. After this pulse or heartbeat threshold test logic 122 is again clocked by blanking logic 106. This third clocking again places the lower output in a logic "1" state and also places the upper output in a logic "1" state. The signal from the lower output again stimulates a 600 msec pulse interval, while the signal from the upper output is applied to pulse width decode logic 62 to cause the pulse width to be seventy-five percent of the selected output pulse width. Thus, on closing the Hall effect switch two normal output pulses at a rate of 100 beats per minute or higher are observed followed by a third pulse at the 100 pulse per minute rate, which pulse is seventy-five percent of the "normal" pulse width. After the narrower pulse threshold test logic 122 is again clocked by blanking logic 106, which signal causes the circuit to reset itself and hold itself reset until the Hall effect switch is again closed.

Figure 3:
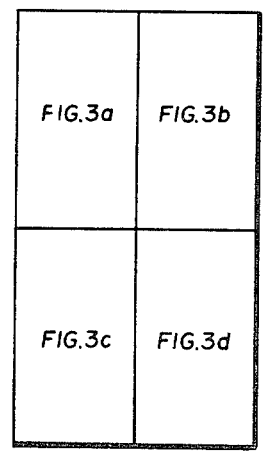
FIG. 3 shows the arrangement of FIGS. 3a through 3d, which in turn show, a more detailed diagram of the digital circuitry of the invention.

Referring now to FIGS. 3a through 3d a more detailed description of each of the blocks shown in FIGS. 2a and 2b will be given, except for blocks 50, 52, 54, and 56 which relate to the mode selection function, which blocks will be discussed in connection with the FIGS. 4 and 6. The arrangement of FIGS. 3a through 3d in order to form a single composite figure is shown in FIG. 3. The circuits shown in FIGS. 3a through 3d are organized in such a manner that all of the logic elements associated with a particular figure block shown in FIGS. 2a and 2b are in the same location and surrounded by a darker line having a number corresponding to the block number in FIGS. 2a and 2b. Insofar as possible, each numbered block in FIGS. 3a through 3d remains in the same relative position to the other numbered blocks as it was in FIGS. 2a and 2b.

The component parts of the circuit shown in FIGS. 3a through 3d include latches, AND gates, OR gates, NAND gates, NOR gates, inverters and transistors.

Figure 3A:
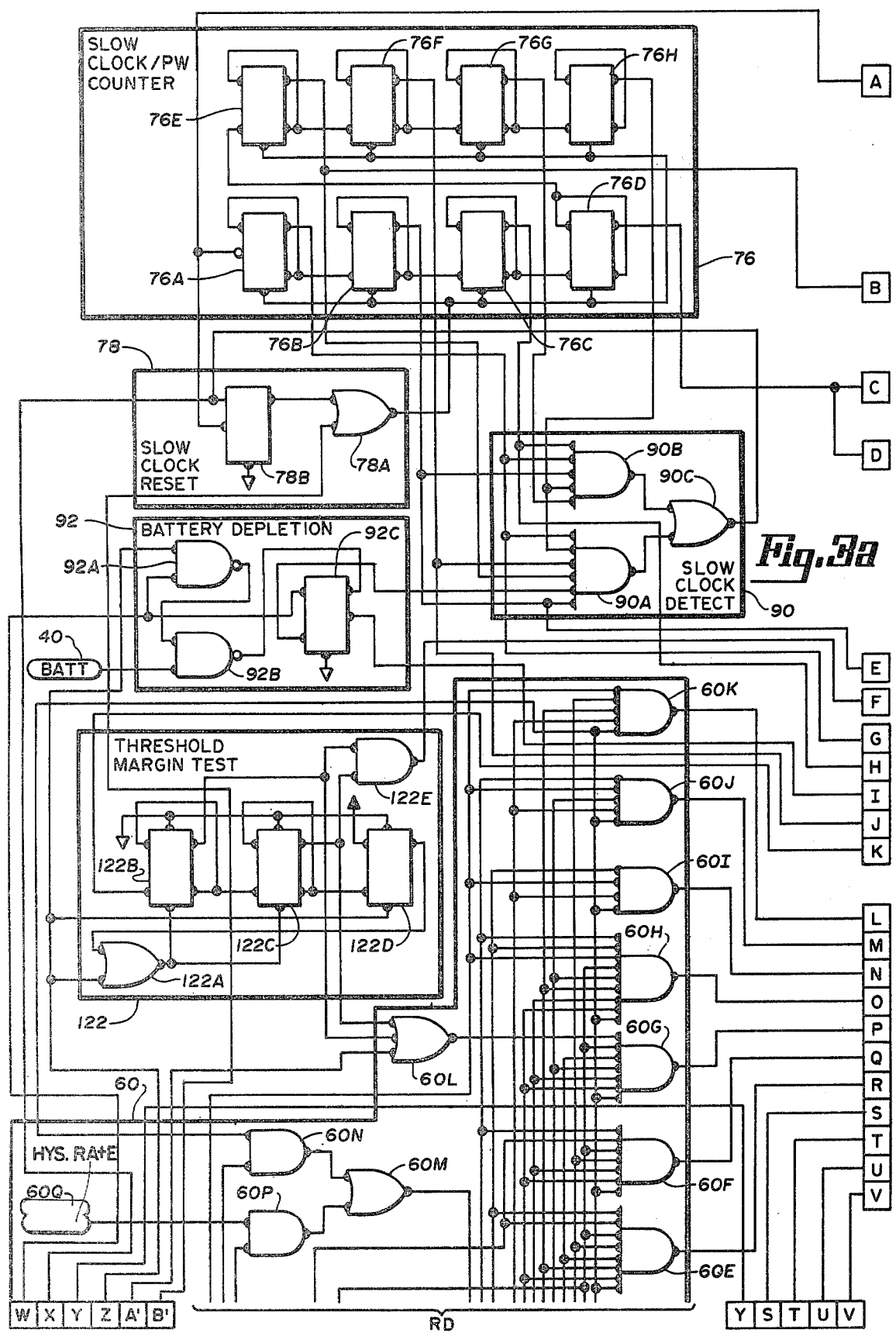

A latch, or flip-flop, as such are commonly referred to, is shown as an element 76E in the upper left-hand corner of FIG. 3a. It is designated as a rectangle having longer verticle sides. Inputs to each latch are normally from the left side with the upper input being a data input and the lower input being a clock input. The outputs of the latch are taken from the right side with the upper output being a conventional "Q", and the lower output being the convention "Q̄" output. For selected latches, a set and/or a reset input are provided with the set input being applied to the top of the rectangle and the reset input being applied to the bottom of the rectangle. In operation, a logic "1" signal applied to the set input causes the "Q" output to assume a logic "1" state and the "Q̄" output to assume a logic "0" state. A logic "1" signal applied to the reset input causes the "Q" output to assume a logic "0" state. Whenever a signal which changes from logic "0" to logic "1" is applied to the clock input, the "Q" output assumes a logic value equal to the logic value of the signal applied to the data input and the "Q̄" output assumes the opposite logic value.

An AND gate is shown schematically as element 90A in FIG. 3a. Such a gate has two or more inputs and one output. The output of an AND gate is a logic "0" signal unless the signals applied to the inputs are all a logic "1", in which case the outputs of the AND gate is a logic "1" signal. A NAND gate is shown as 92A in FIG. 3a. Such a gate also has two or more inputs and one output. The output is a logic "1" signal unless the signal applied to each of the inputs is a logic "1", in which case the output is a logic "0" signal.

An OR gate is shown schematically as element 78A in FIG. 3a. Such a gate has two or more inputs and one output. The signal at the output of an OR gate is a logic "1" if any of the signals applied to the input is a logic "1", and is a logic "0" only in a case where all of the signals applied to the inputs are a logic "0".

Figure 3B:
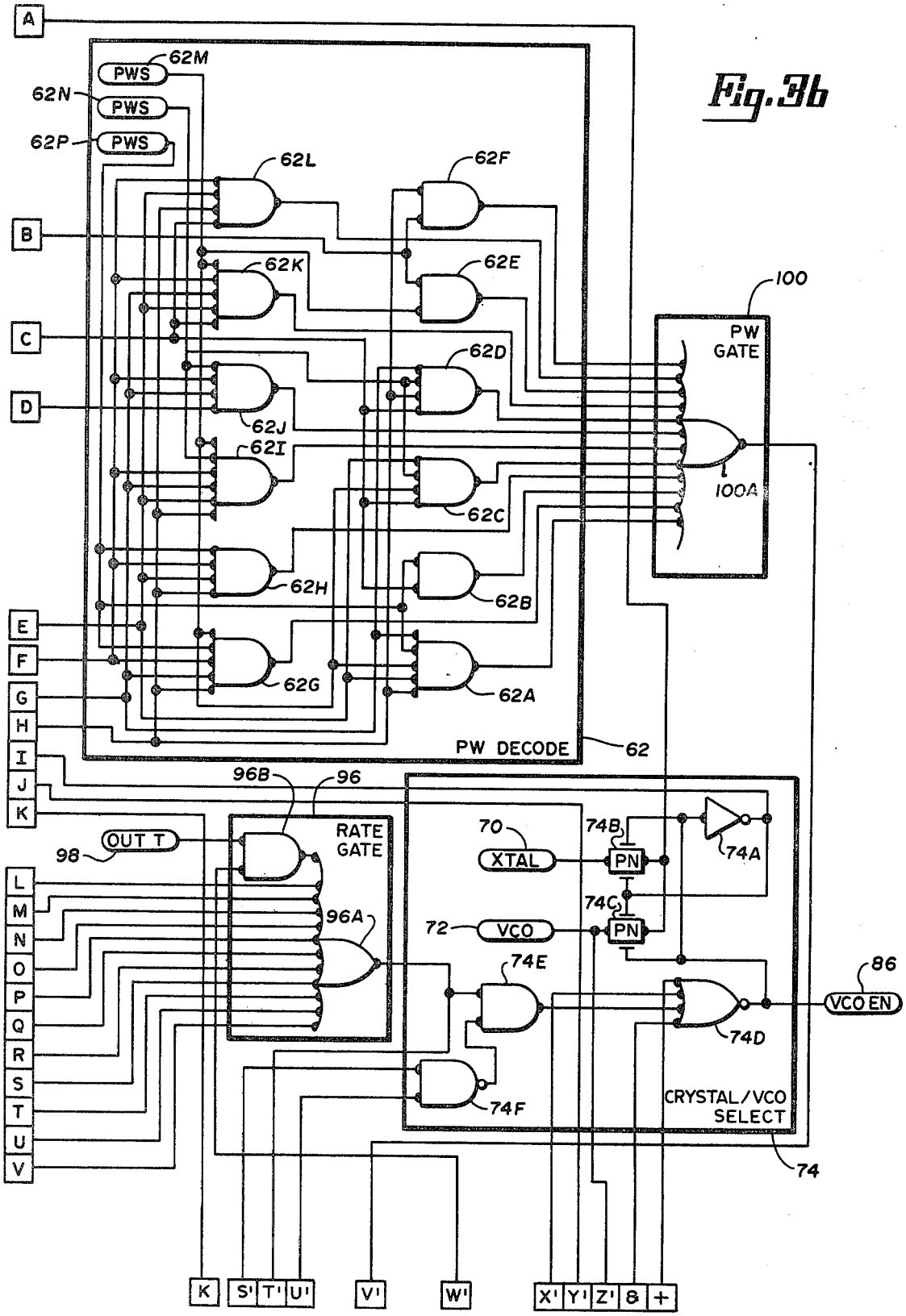

A NOR gate is shown schematically as element 74D in the lower portion of FIG. 3b. It has two or more inputs and one output. The signal at the output of a NOR gate is normally a logic "0" unless the signals supplied to each of the inputs are all a logic "0" in which case the signal at the output is a logic "1".

An inverter is shown schematically as element 74A in the lower righthand side of FIG.-3b. Such an element has one input and one output with the output providing a signal having a logic value opposite to that of the signal applied to the input.

Transmission gates are shown schematically at 74B and 74C in FIG. 3a, 74B each being composed of two transistors, an n-channel and a p-channel transistor. In the circuit shown the gates act simply as bilateral switches. In each switch there are two terminals indicated by the darkened half-circles, which terminals can be the inputs or outputs since current will flow both ways through the switch; in the application shown however signals are applied so they flow only from left to right. The control voltages are applied to the gates of the transistors which are shown in the drawing as the upper and lower terminals of the transmission gates with the logic value of the signal applied to the upper terminal of each transmission gate being opposite in value to the logic value of the signal applied to the lower terminal of the transmission gate. When the common line between the transmission gates goes to a logic "1" value the p-channel transistor in the upper transmission gate 74B turns off while the n-channel in the lower transmission gate 74C turns on; at the same time the logic "0" signal applied to the upper terminal of gate 74B turns off the n-channel transistor of that gate which the logic "0" signal applied to the lower terminal of gate 74C turns on the p-channel transistor of that gate. When the signal on the common line goes to logic "0" the transmission gate 74B turns on while the transmission gate 74C turns off.

As stated above, the conventional provisions of power supply voltages and ground are not shown in the circuit. However, applications of power supply voltage and ground are shown when they are applied to the input of a latch. A power supply voltage is shown schematically at 82A in the lower lefthand corner of FIG. 3c, while the ground is shown schematically at 82B in the same figure. The ovals bearing a written lable, such as at 40 in FIG. 3a refer to output or inputs, usually to the analog circuit, as described above. The oval bearing no written lable, such as at 60Q in the lower lefthand corner of FIG. 3a refer to outputs from the mode selection circuitry, which shall be described in more detail below in connection with the discussion of FIGS. 4 and 5.

The detailed circuitry in FIGS. 3a through 3d shall be explained in roughly the same order in which the circuit blocks were discussed above. Referring to FIG. 3b the crystal/VCO select circuit is shown at 74. It consists of inverter 74A, the two transmission gates 74B and 74C, NOR gate 74D, AND gate 74E, and NAND gate 74F. NOR gate 74D is responsive to inputs from rate gate 96 (via AND gate 74E), from output logic 86, and to two inputs from amp reset 84. If any of these inputs are a logic "1", the output of NOR gate 74D becomes a logic "0". This logic "0" enables the VCO oscillator in analog circuit 14 through VCO ENABLE output 86. This signal is also applied to the upper terminal of transmission gate 74B and the lower terminal of transmission gate 74C, and is applied to the input of inverter 74A thereby causing a signal of the opposite value, a logic "1" in this instance to be applied to the common line of the transmission gates. With this bias the transmission gate 74C will conduct while the transmission gate 74B will not conduct, causing the circuit to "select" the VCO oscillator signal for its output. If all the inputs to NOR gate 74D are made logic "0" its output is a logic "1" signal. This signal disables the VCO oscillator through VCO ENABLE output 86 and causes a logic "1" signal to be applied to the "non-common" terminals of transmission gates 74B and 74C while a logic "0" signal is applied to their common line. This causes the transmission gate 74B to conduct and the transmission gate 74C to not conduct, hereby "selecting" the crystal oscillator signal for the oscillator output of the circuit. The signal from rate gate 96 is gated through AND gate 74E. This signal is blocked if the input to gate 74E from AND gate 74F is a logic "0" which, in turn, is the case only if both of the inputs to gate 74F are logic "1". One of these inputs is applied from output logic 80 and the other from RATE LIMIT output 112. As will be seen from the discussion below of the output logic circuit, both of the inputs are logic "1" only during the period in which an output pulse has been called for, but the pulse has been held in abeyance by a RATE LIMIT signal. This, in effect, prevents the rate gate signal from being applied to NOR gate 74D during this period, and thus prevents the VCO oscillator from being enabled, which would unnecessarily consume power during a period in which the VCO oscillator is not needed.

The output selected by crystal/VCO select 74 is applied to slow clock/PW counter 76 in FIG. 3a. Slow clock/PW counter 76 is comprised of eight flip-flops 76A through 76H. The oscillator signal from crystal/VCO select 74 is applied to the clock input of flip-flop 76A. The "Q" output of each flip-flops 76A through 76H is applied to its own data input and is also applied to the clock input of the next succeeding flip-flop. The reset input of each of the flip-flops 76A through 76H is responsive to the output signal of OR gate 78A in slow clock reset 78. The "Q" output of fliop-flops 76A through 76H are applied to the slow clock detect 90, pulse width decode 62, and the recharge 116 circuits as shall be described below.

Slow clock detect logic 90 includes AND gates 90A and 90B and OR gate 90C. The "Q" output of flip-flops 76A, 76B, 76E, 76F, and 76H in the slow clock/PW counter 76 circuit are applied to the inputs of gate 90A. The "Q" output of latch 92C in battery depletion circuit 92 is also applied as input to gate 90A. If the latter input is a logic "1" then the output of gate 90A will become a logic "1" when the "Q" output of flip-flops 76A, 76B, 76E, 76F and 76H are all a logic "1". This condition is first reached after 179 oscillation pulses have been applied to the clock input of latch 76A. The output of gate 90A is applied to the input of OR gate 90C, thus when the output of gate 90A becomes logic "1" the output of gate 90C also becomes a logic "1". This signal is applied to the data input of latch 78B in slow clock reset logic 78. The clock input of latch 78B is responsive to the oscillator output of crystal/VCO select logic 74. Thus, on the next oscillation after the output of OR gate 90C becmes a logic "1" the "Q" output of latch 78B is clocked to a logic "1" state. This output is applied to OR gate 78A, which becomes logic "1" in response to the same logic value being applied its input. As mentioned above, the output of OR gate 78A is applied to the reset inputs of flip-flops 76A through 76H in slow clock/PW counter 76. Thus, the logic "1" output of gate 78A causes flip-flops 76A through 76H to be reset so that all its "Q" outputs are 0, and a new slow clock cycle begins on the next oscillator pulse applied to the clock input of latch 76A. The "Q" outputs of flip-flops 76A, 76B, 76C, 76G and 76H are applied to the inputs of AND gate 90B. These outputs are all a logic "1" only after 199 oscillator pulses have been counted by slow clock/PW counter 76. Normally this count will not be reached since flip-flops 76A through 76H will be reset after 179 clock cycles. However, if the "Q" output of latch 92C is a logic "0" then the output of gate 90A will remain a logic "0" and counter 76 will continue counting until 199 oscillator cycles have been counted, whereupon the output of gate 90B will become a logic "1". This output signal is applied to OR gate 90C and flip-flops 76A through 76H are reset through slow clock reset circuit 78 as described above.

Figure 3C:
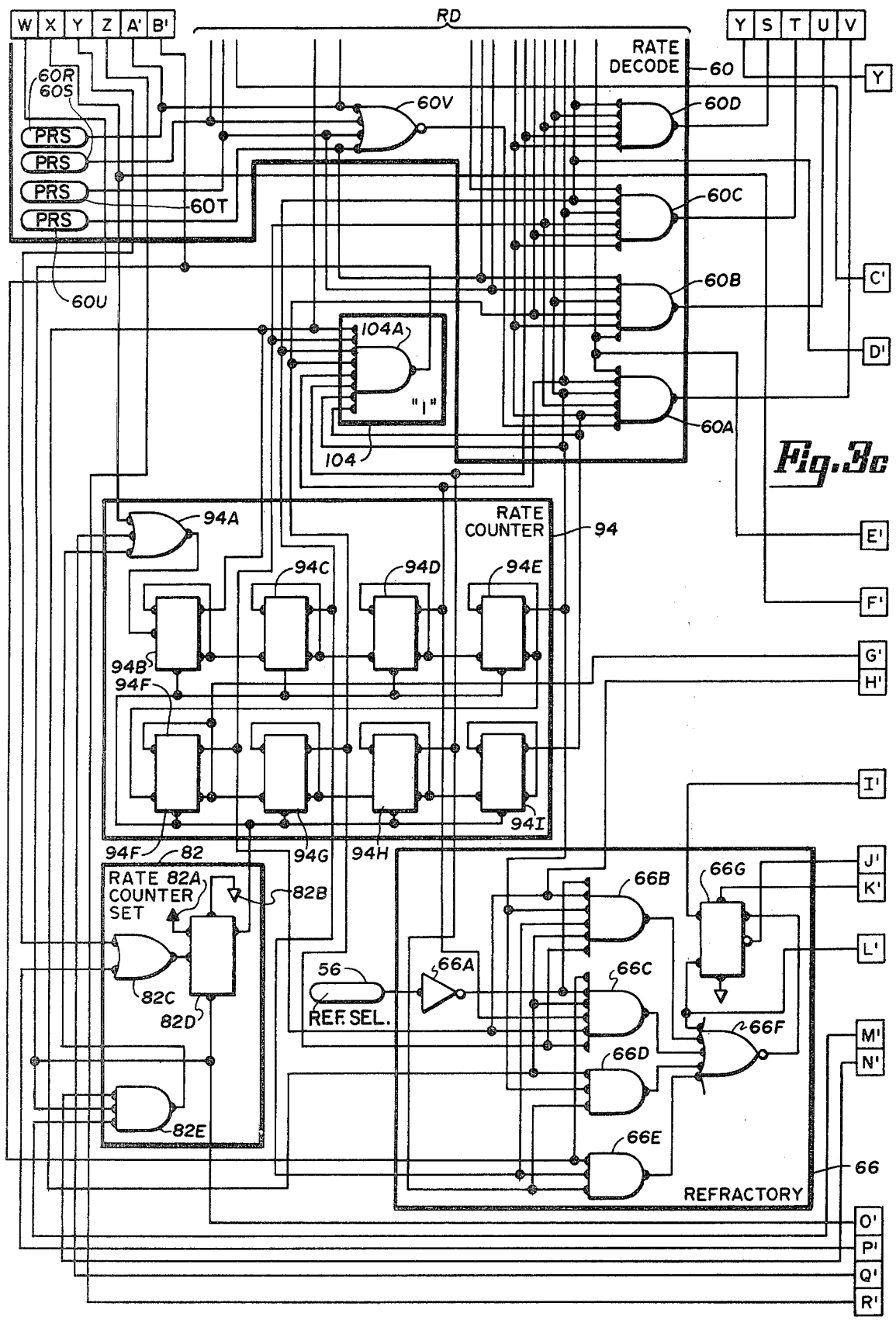

Rate counter 94 in FIG. 3c is composed of OR gate 94A and eight latches 94B through 94I. The output of OR gate 90C in slow clock detect logic 90 is applied as one input to OR gate 94A. The output of gate 94A is applied to the clock input of latch 94B. Thus, each time the output of gate 90C goes from a logic "0" to a logic "1" at the end of a slow clock cycle, the output of gate 94A will also go from a logic "0" to a logic "1" and latch 94B will be clocked. The "Q" output of each of latches 94B through 94I is applied to its own data input and is also applied to the clock input of the next succeeding latch, as is usual for binary counters. The "Q" outputs of some or all of the latches 94B through 94I are applied to rate decode logic 60, counter "1" detect gate 104, blanking logic 106, recharge logic 116, and refractory logic 66 circuits as shall be described below.

Rate decode logic 60, shown in FIGS. 3a and 3c comprises ANd gates 60A through 60K, OR gate 60L. NOR gates 60M and 60U, AND gates 60N and 60P and outputs 60Q through 60U from the rate selection circuitry 50. The "Q" outputs of several of latches 94B through 94I in rate counter circuit 94 are applied as inputs to each of gates 60A through 60K. For example, gate 60A has inputs from the "Q" output of latches 94D, 94E, 94F, and 94I, gate 60D has inputs from the "Q" outputs of latches 94C, 94E, 94F, 94H, and 94I and gate 60G has inputs from the "Q" output of latches 94D, 94E, 94G and 94H. All of gates 60A through 6K except for gate 60D also have inputs from some or all of outputs 60Q through 60U from rate select circuitry 50, and from the "Q" output of latch 64C in hysteresis logic 64. Gate 60D is the 50 pulses per minute gate; that is, when rate counter 94 has counted approximately 218 slow clock pulses equivalent to a time period of 1.2 seconds the "Q" output of latches 64C, 64E, 64F, 64H, and 64I will all be a logic "1" and thus the output of gate 60D will go to a logic "1" which signal will operate on rate gate 96 to initiate an output cycle as will be discussed below. Since the 50 pulse per minute rate is the slowest rate gated by any of the gates, 60A through 60K, the 218 slow clock cycle count required to enable gate 60D will be reached only if none of the other gates are enabled, otherwise, as will be seen, the rate counter will be reset before this count is reached. Gate 60D is not connected to rate select 50 or hysteresis 64 so that it will always be enabled as a safety feature. Thus, if the rate selection circuitry fails the 50 bpm rate will take over ensuring that the pacemaker does not fall below this rate.

The details of the rate selection circuitry will be discussed below in connection with FIGS. 4 and 5. As will be shown in that discussion, outputs 60Q through 60U each can be placed in either a logic "0" state or a logic "1" state by means of the mode selection operation. Input 60Q is the hysteresis pulse rate select input and inputs 60R through 60U are the "normal" pulse rate selection inputs. Each of the inputs 60R through 60U are applied to one or more of latches 60A, 60B, 60C, and 60E through 60K in rate decode logic 60. This circuit is essentially a four-line to ten-line decoder. That is, the four inputs 60R through 60U are considered to be a series of four binary digits and the connections between the inputs and gates 60A, 60B, 60C, and 60E through 60K are such that each configuration of input values that corresponds to a decimal number from one to ten in binary notation enables a single gate. For example, the configuration of input values that corresponds to the binary representation of the decimal number 6, i.e. 0110, corresponds to the inputs 60R, 60S, 60T, and 60U having the values logic "0", logic "1", logic "1" and logic "0" respectively and results in gate 60I only being enabled by the outputs of rate select 50. The connections between latches 94B through 94I, and gates 60A through 60K are such that a single gate is enabled each time rate counter 94 reaches a count corresponding to a time period resulting in a pulse rate of 50, 60, 65, 70, 75, 80, 85, 90, 100, 110, and 120 beats per minute. The connections between inputs 60R through 60U and gates 60A through 60K are such that the binary code for the decimals one through ten enable the gates governing the rates 50, 60, 65, 75, 80, 85, 90, 100, 110, and 120 respectively. An eleventh rate is selectable by means of NOR gate 60V. The four inputs 60R through 60U are applied to the inputs of NOR gate 60V and the output of the gate is applied to AND gate 60A. Thus, when the four inputs 60R through 60U are all zero (corresponding to binary notation for a decimal zero) gate 60A is enabled. It is noted that the signal from input 60R passes through OR gate 60L before being applied the 100 pulse per minute gate 60G. This does not change the function as described above, but merely allows the gate to be activated during the threshold margin test period, as will be discussed below, in addition to being activated if 100 beats per minute is selected as the basic rate for the pacemaker. It is also noted that the signal from input 60T passes through AND gate 60N and OR gate 60M before being applied to gate 60C, which is the gate for the 60 beat per minute rate, one of the two hysteresis rates. This also does not essentially change the operation of that gate as discussed above, but permits the 60 beat per minute rate to be activated during hysteresis, as will be discussed below. Finally, it is noted that the input 50U, which corresponds to the first binary digit, is not connected to gate 60D, the gate governing the 50 beat per minute rate, as it would be in order to be enabled only when the binary digit 0001 is coded into the inputs 60R through 60U. This connection is omitted in order that the 50 beat per minute gate will always be enabled, as a safety feature as discussed above.

When one of gates 60A through 60K is enabled both by outputs 50R through 50U and by rate counter 94 all its inputs become a logic "1" and its output therefore changes from logic "0" to a logic "1", except in the case when the hysteresis function is operating, which case shall be discussed below. In normal operation, a specific one of gates 60A through 60K is enabled through inputs 60R through 60U, and the rate counter 94 advances in response to pulses from slow clock detect logic 90 as discussed above until the count corresponding to the selected gate is clocked, whereupon the output of the gate goes to logic "1". All of the outputs from gates 60A through 60K are applied to OR gate 96A (FIG. 3b), thus if the output of any one of gats 60A through 60K goes to a logic "1" then the output of gate 96A also goes to a logic "1". Output trigger 98 is applied to one input terminal of AND gate 96B in rate gate circuitry 96. The other terminal of AND gate 96B is responsive to the "Q" output of latch 80B in the output logic circuitry 80. As will be discussed below, this output is a logic "1" whenever the output pulse is not being called for, including the period when the rate limit function is operating. This permits the forcing of the pulse generator into rate limit via the output trigger as discussed above.

The output of gate 96A is applied to one of the inputs of ANd gate 74E in crystal/VCO select logic 74 and to the data input of latch 86A in output logic 80. The other input of gate 74E is provided from the output of gate 74F, which output is logic "0" only during the period when the rate limit function is operating, as discussed above. If the pacemaker is not in rate limit then the output of gate 74E becomes a logic "1" when any of rate decode gates 60A through 60K becomes a logic "1". The output of gate 74E is applied to NOR gate 74D to enable the VCO oscillator as discussed above.

Figure 3D:
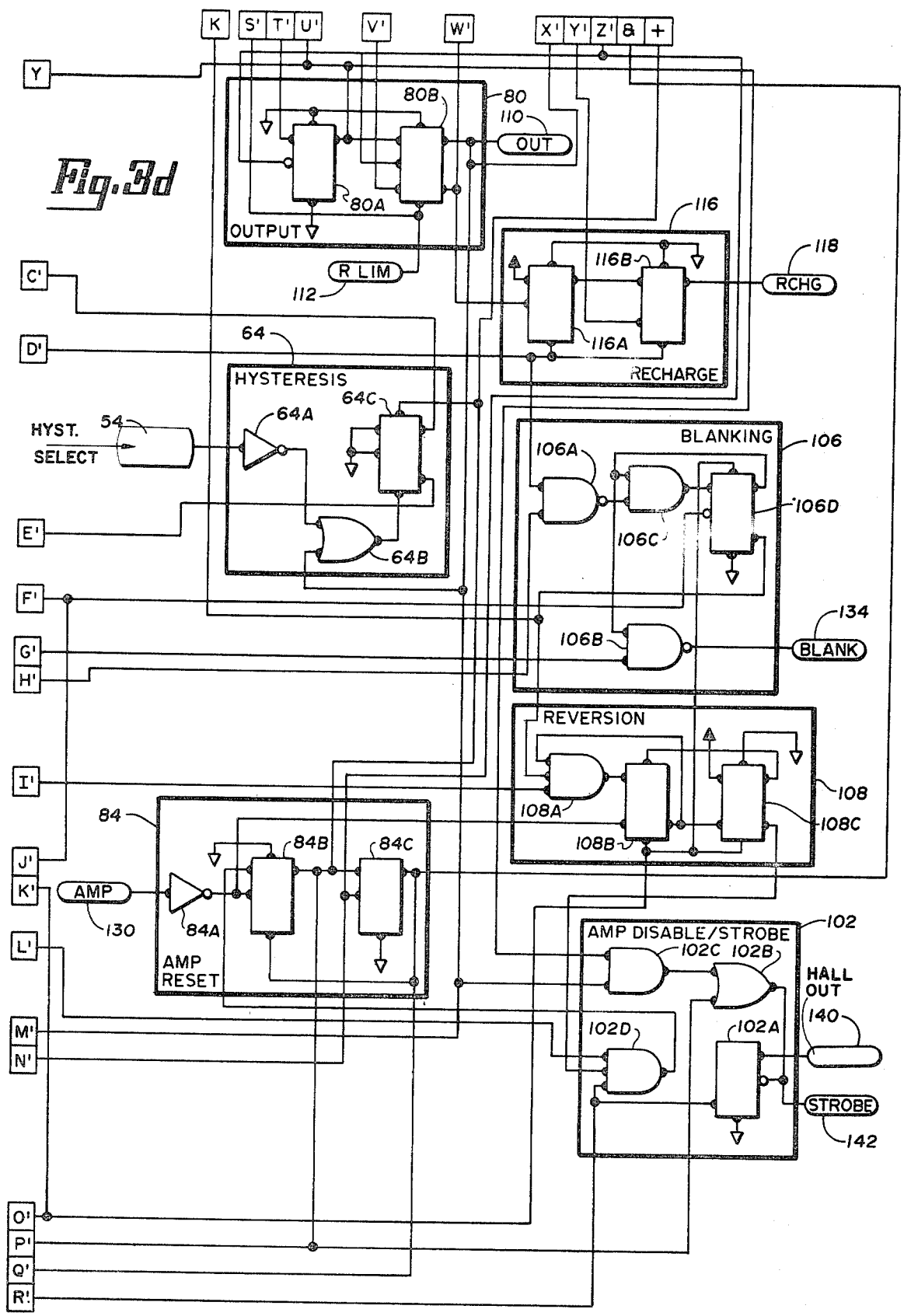

Output logic 80 in FIG. 3d consists of flip-flops 80A and 80B. As mentioned above, the data input of flip-flop 80A responds to the output of gate 96A and rate gate circuitry 96. The clock input of the same flip-flop responds to the oscillator output of the VCO output 72. On the first VCO pulse after the VCO oscillator is activated by the signal from gate 96A to the "Q" output of flip-flop 80A is clocked to a logic "1" state. This signal is applied as one of the inputs to OR gate 82C in rate count set 82 in FIG. 3c. Rate count set 82 comprises OR gate 82C, latch 82D, and AND gate 82E. In response to the signal from the "Q" output of latch 86A, OR gate 82C clocks latch 82D so that its "Q" output goes to a logic "1" state. This signal is applied to the set input of latches 94B through 94I (shown in this case at the bottom of the latches) to set all the "Q" outputs of the latches to a logic "1" state. The "Q" outputs of the latches are all applied to the input of AND gate 104A which comprises the counter "1" detect gate 104. When all the latches 94B through 94I are set so that the "Q" outputs go logic "1", the output of gate 104A in turn goes to a logic "1" and is applied to the reset input of latch 82D in the rate counter set circuit 82 to reset the "Q" output of latch 82D to a logic "0" state. It is also applied to one of the inputs to OR gate 78A in the slow clock reset circuit 78 to reset the slow clock/PW counter latches 76A through 76H as discussed above. The "all 1's" signal from gate 104A is also applied to several other gates in the blanking, reversion and refractory logic which shall be discussed later.

Returning now to the operation of the output logic 80 in FIG. 3d, the "j" data input of latch 80B is responsive to the "Q" output of latch 80A, while the clock input is responsive to VCO output 72. On the next VCO oscillation after the "Q" output of latch 80A goes to a logic "1", the "Q" output of latch 80B is clocked to a logic "1", while the "Q" output goes to a logic "0". The logic "1" signal from the "Q" output is applied to output to the analog circuit to initiate the pulse generator output. The same signal is applied to NOR gate 74D in crystal/-VCO select circuitry 74 to continue the enabling of the VCO oscillator as discussed above for the duration of the output pulse. The signal is also applied to AND gate 82E in rate count set logic 82. The middle input of the same gate is responsive to the output of "all 1's" gate 104A which went to a logic "1" on the previous VCO cycle. The third input to gate 182E is responsive to the VCO output 72, thus on the next VCO oscillation all three inputs are a logic "1" and the output also becomes a logic "1". This output signal is applied to gate 94A to clock latches 94B to 94I as discussed above. Since the latches were in the "all 1's" condition this clock pulse advances them to the overflow condition.

Returning again to the output logic circuit 80 in FIG. 3d, rate limit output 112 from the analog circuit 114 is applied to the reset input of latch 80B. If the rate limit function is operating this signal will be a logic "1" and it will hold latch 80B reset for the rate limit period. Thus the "Q" output of latch 80B will remain at a logic "0" and the output pulse and the resetting of the rate counters will be postponed. During this time the "Q" output of latch 80A will remain at a logic "1" since its input from the rate gate circuit 96 remains at a logic "1" because all the "Q" outputs of latches 94B through 94I are at a logic "1" condition. When the rate limit period comes to an end output 112 goes to a logic "0" and on the next VCO oscillation the "Q" output of latch 86B is clocked to a logic "1" to initiate the output cycle.

As mentioned above, the output 112 is also applied to one input of gate 74F. Since the other input to this gate is from the "Q" output of latch 80A, during the time the rate limit is holding the output pulse in abeyance both inputs to this gate are a logic "1" and thus the output is a logic "0". This output is applied to one of the inputs of AND gate 74E to disable the VCO oscillator during this period as discussed above.

The duration of the output pulse is determined by the pulse width decode circuitry 62 which comprises AND gates 62A through 62L and outputs 62M, 62N and 62P. These three outputs are from the pulse width selection circuitry which is the subject of copending U.S. Patent Application Ser. No. 98,159, which is hereby incorporated by reference. These outputs each assume either a logic "0" or a logic "1" state as a result of the mode selection operation discussed with reference to FIGS. 4 and 5 in the above stated application Ser. No. 98,159. Like the outputs 60R through 60U in the rate decode circuitry 60, outputs 62M through 62P can be considered as a series of binary digits, except in this case there are three rather than four digits. Gates 62A through 62L are divided into two banks of gates the first being 62A through 62F and the second being 62G through 62L. The second bank is enabled only during the threshold test cycle and will be discussed below in connection with threshold margin test circuitry 122.

The operation of the pulse width decode circuitry 62 in conjunction with counter 76 is similar to the operation of the pulse rate decode circuitry 60 together with the counter 94. Each gate 62A through 62F has one or more inputs from the "Q" outputs of latches 76A through 76E so that the gates are enabled at counts corresponding to time periods of 0.35, 0.4, 0.5, 0.65, 0.8, and 1.0 msec. respectively. The inputs to gates 62A through 62F from outputs 62M through 62P are such that the circuit forms a three-line to six-line decoder. Each combination of logic states of outputs 62M through 62P that corresponds to the binary representation for the decimal numerals one through six enables one and only one of gates 62A through 62F. The connections are such that the code for the numerals zero through five selects the pulse widths 0.1, 0.8, 0.65, 0.5, 0.4, and 0.35 msec respectively, except that there is no connection between outputs 62M through 62P and the 1.0 msec gate, 62F, so that this gate will always be enabled with respect to pulse selection circuitry 52 as a failsafe measure. The outputs of each of gates 62A through 62F are provided to OR gate 100A. In operation, slow clock/PW counter 76 counts oscillations until it reaches the count which enables the one of gates 62A through 62F which is also enabled by pulse width select circuitry 54. All the inputs of that gate will then be a logic "1" and therefore the output will also change to a logic "1", which output applied to gate 100A causes the output of that gate to become a logic "1" which output is in turn applied to the "K" data input of latch 80B in the output circuitry 80. On the next VCO clock cycle the "$\overline{Q}$" output of latch 80B is clocked to a logic "1" state and the "Q" output to a logic "0" state. The latter signal disables the output pulse through output 110, disables the VCO oscillator and selects the crystal oscillation through NOR gate 74D in crystal/VCO select circuitry 74, and disables gate 82E in rate counter set circuit 82 terminating the reset cycle.

Recharge logic 116 comprises latches 116A and 116B. The data input of latch 116A is always held at a logic "1" and its clock input is responsive to the "$\overline{0}$" output of latch 80B.

The logic "1" signal from the "$\overline{Q}$" output of latch 80B clocks latch 116A which changes its "Q" output to a logic "1". A short time later the "Q" output of latch 76F in slow clock/PW counter 76 goes to a logic "1" and clocks latch 116B changing its "Q" output to a logic "1". This signal initiates the recharge interval through output 118. About 10 msec later the "Q" output of gate 94C in rate counter 94 goes to a logic "1" which resets both latches 116A and 116B causes the "Q" output of gate 116B to go to a logic "0" terminating the recharge interval. The "$\overline{Q}$" output of latch 80B also is applied to gate 96B in rate gate circuitry 96 enabling the output trigger to force the pulse generator into rate limit when an external signal is applied, as discussed above.

Battery depletion logic 92 comprises NAND gates 92A and 92B and latch 92C which is reversed in position from the usual position of latches so that its inputs are on the right and its outputs are on the left. Battery output 40 is applied to one of the inputs of NAND gate 92B. The "$\overline{Q}$" output of latch 102A in amp disable/strobe circuitry 102 is applied as one of the inputs of gate 92A. As will be discussed below, this latter input is a logic "0" when the Hall effect switch is closed and is a logic "1" otherwise. If the Hall effect switch is closed at least one of the inputs of gate 92A will be a logic "0" and thus, its output will be a logic "1". If the battery is not depleted the output of output 40 is also a logic "1". Thus both the inputs of gate 92B will be a logic "1" and therefore its output will be a logic "0". The clock input of battery depletion logic 92C is responsive to the inversion of the VCO ENABLE signal from crystal/VCO select 74 and its data input is responsive to the output of gate 92B. Thus on the first VCO ENABLE pulse after the closing of the Hall effect switch the "Q" output of latch 92C will remain at a logic "0" state if the battery is not depleted. This output is applied as one of the inputs to gate 92A maintaining its output at a logic "1" even after the Hall effect switch is opened. Thus, as long as battery output 40 stays at a logic "1" that is, as long as the battery remains undepleted, the output of gate 92B will remain a logic "0" and the circuit will remain latched with the "Q" output of gate 92C in the logic "0" position. If the battery becomes depleted, the output of battery output 40 becomes a logic "0" causing the output of gate 92B to go to a logic "1" and on the next VCO ENABLE pulse the output of latch 92C goes to a logic "1". Thus, as long as the Hall effect switch remains open both inputs to gate 92A remain a logic "1". Thus the output of latch 92A will be a logic "0" which signal applied to the input of gate 92B keeps the output of that gate at a logic "1" keeping the circuit latched with the "Q" output of latch 92C in the logic "1" state, even if the battery returns to a nondepleted condition. However, when the Hall effect switch is closed the upper input to gate 92A goes to a logic "0", the output of the gate goes to a logic "1" whereupon the output of latch 92B will become a logic "0" if the battery is in the nondepleted state latching the circuit back into the nondepleted output state. If the battery is still depleted when the Hall effect switch is closed then output 40 will be at a logic "0", the output of gate 92B will remain at a logic "1" and the circuit will remain latched in the "depleted" output state. From the above it is seen that when the battery is in a nondepleted state the "$\overline{Q}$" output of latch 92C is latched in the logic "1" condition and when the battery is depleted it is latched in the logic "0" condition. This signal is applied to gate 90A in slow clock detect logic 90. Thus, the battery depletion signal will disable gate 90A allowing gate 90B to trigger the slow clock output signal from gate 90C extending the period of the slow clock by eleven percent as discussed above.

Amp reset logic 84 in FIG. 3d comprises inverter 84A and flip-flops 84B and 84C.

As will be seen below, the data input to latch 84B is a logic "1" whenever the hysteresis function, reversion function, or the Hall effect switch is not disabling the demand function of the pacemaker. The output of amp output 130 is applied to the clock input of latch 84B through inverter 84A. Thus, when a heartbeat is sensed the clock output goes from a logic "0" to a logic "1" clocking the "Q" output of latch 84B to a logic "1" state. This signal is applied to the input of OR gate 82C (FIG. 3c) causing latches 94B through 94I to be set to the "all 1's" condition as described above. The signal is also applied to gate 74D in crystal/VCO select logic 74 enabling the VCO oscillator as discussed above. In addition the signal also is applied to gate 102B in amp disable/strobe logic 102 to provide the strobe output which shall be discussed below. The clock input of latch 84C is responsive to VCO output 72 while the data input of the same latch is responsive to the "Q" output of latch 84B. Thus on the first VCO oscillation after the latter input goes to logic "1" the "Q" output of latch 84C is in turn clocked to a logic "1" state. This signal is applied to latch 74D to maintain the operation of the VCO oscillator. It is also applied to the input of gate 94A to clock latches 94B through 94I to the overflow condition. Finally it is applied to the reset input of latch 84B changing the "Q" output of that latch to a logic "0". On the next VCO oscillation the "Q" output of latch 84C is clocked to a logic "0" turning off the VCO oscillator, and removing the reset signal from latch 84B readying the circuit for the next cycle.

Blanking logic 106 comprises NAND gates 106A and 106B, AND gate 106C, and flip-flop 160D. The set input of latch 106D is responsive to the output of "all 1's gate" 104A. This signal becomes a logic "1" at the beginning of an output cycle and immediately after a natural heartbeat is sensed so that the "Q" output of the latch goes to a logic "1" and the "$\overline{Q}$" output goes to a logic "0". The logic "1" output is applied to one of the inputs of AND gate 106C and one of the inputs of NAND gate 106B. The inputs to gate 106A are responsive to the "Q" output of latches 94C and 94F in rate counter 94. Within one VCO oscillation after the "all 1's" condition these latches are clocked to the overflow state so that both the inputs to gate 106A go to a logic "0" and the output goes to a logic "1". Both inputs to gate 106C are then a logic "1" and the output is thus also a logic "1". On the next slow clock pulse gate 106D is clocked but remains latched with its "Q" output at logic "1" since its inputs is also a logic "1". The "Q" output of latch 106D is also applied to one of the inputs of NAND gate 106B. The other input of this gate is responsive to the "Q" output of latch 94F in the rate counter circuit 94. When latches 94B through 94I are clocked to the overflow condition the "Q" output of latch 94F goes to a logic "1". Thus, both inputs to gate 106B are a logic "1" at this time and the output is a logic "0". This logic "0" signal enables the external blanking through output 134 to analog circuit 14. The "Q" output of latch 106D provides the internal (i.e. within the digital circuit) blanking signal which goes to reversion logic 108 and threshold test logic 122. Approximately 90 msec after the initiation of the blanking period by the set signal from the "all 1's" gate 104A, the "Q" output of latch 94F goes to a logic "0", which causes the output of gate 106B to go to a logic "1" which terminates the external blanking. Approximately 10 msec later the "Q" outputs of latches 94C and 94F will both be a logic "1", thus the output of latch 106A will go to a logic "0" which, in turn, causes the output of gate 106C to also go to a logic "0" state. On the next slow clock pulse the "Q" output of latch 106D is clocked to the logic "0" state while the "Q" output is clocked to a logic "1" state which terminates the internal blanking period. The internal blanking period is made slightly longer than the external blanking period in order to assure that any spurious pulses that may have appeared in the amplifier circuit in analog circuit 18 during the blanking period will be dissipated by the time the internal blanking goes off.

Amp diable/strobe logic 102 comprises latch 102A, OR gate 102B, and AND gates 102C and 102D. Latch 102A is drawn with its inputs on the right and its outputs on the left, the reverse of the normal input/output representation for a latch. One input to gate 102C is from the "Q" output of latch 80A in output circuit 80, while the other input is from the "Q" output of latch 80B in the same circuit. The output of gate 102C thus goes from logic "0" to logic "1" when the "Q" output of latch 80B goes to logic "1" to initiate the output pulse. On the same VCO oscillation rate gates 94B and 94I are clocked to the overflow condition by means of gates 82E and 94A, which places a logic "0" signal on the input of gate 80A through gates 60A through 60K and gate 96A. On the trailing edge of the same VCO pulse, latch 80A is clocked so that its "Q" output goes to a logic "0", which in turn changes the output of gate 102C back to a logic "0". Thus, the output of gate 102C is a logic "1" only for a period equal to approximately one-half of a VCO oscillation, or about 25 microseconds. This output is applied through gate 102B to strobe output 142 to produce the 25 microsecond strobe pulse each time the pulse generator output is called for. If a pulse generator output is not called for because a natural heartbeat is detected then a logic "1" strobe output is produced from gate 102B during the time period in which the "Q" output is latch 84B and amp reset circuit 84 is logic "1". As described above, this output goes from logic "0" to a logic "1" and back to a logic "0" within a time period equal to at most the time period during which the VCO oscillator is at a logic "0" or one-half of a VCO cycle, and thus a 25 sec strobe pulse is also produced each time a heartbeat is detected by amp reset circuit 84. The strobe output of gate 102B is also applied to an inverted clock input to latch 102A. The data input of latch 102A is responsive to Hall effect 140. As mentioned above, this output is a logic "1" only during the time period in which Hall effect switch 32 is closed as described in reference to FIG. 4. Thus, on the trailing edge of the first strobe pulse after Hall effect switch 32 is closed the "Q" output of latch 102A will be clocked to a logic "0" state. This logic "0" signal is applied to NAND gate 92A in battery depletion circuit 92 to "unlatch" the circuit as described above. It is also applied to gate 122A and latch 122D in threshold margin test circuit 122 to initiate the threshold margin test function as shall be described below. Finally it is applied to one of the inputs of gate 102D. Gate 102D is the amp disable gate, that is, its output is applied to the data input of latch 84B in amp reset circuit 84. Whenever any of the inputs of gate 102D go to a logic "0" its output goes to a logic "0" and the amp reset cycle is disabled, that is it will not reset the rate counter as discussed above. Thus, when the Hall effect switch is closed and the "Q" output of gate 102A goes to a logic "0" the amp reset function is disabled. The other two inputs to gate 102D are from reversion circuitry 108 and the refractory circuitry 66, which circuits shall be discussed below.

Refractory logic 66 comprises inverter 66A, AND gates 66B through 66E, NOR gate 66F, and latch 66G. The inputs and outputs to latch 66G are reversed from the normal position, that is the inputs are applied on the right and the outputs emerge from the left. The set input to latch 66G is responsive to the output of "all 1's" gate 104A. As discussed above, this output goes to a logic "1" just prior to an output pulse and immediately after a natural heartbeat is detected. These logic "1" signals set latch 66G so that its "Q" output goes to a logic "1" and its "Q" output goes to a logic "0". The "Q" output is applied to the reversion circuitry and shall be discussed below. The "Q" output is applied to one of the inputs of the amp disable gate 102D in amp disable/strobe circuitry 102. The logic "0" signal causes the output of gate 102D to become a logic "0" and to disable the amp reset function as described above. The "Q" output is also applied as one of the inputs to gate 66F. The other inputs to this gate are from AND gates 66B through 66E. The inputs of these latter gates are from the "Q" outputs of latches 94B through 94I, which outputs go to a logic "0" within a VCO cycle of the "all 1's" condition. The clock input to latch 66G is from the slow clock output; the latch is clocked on the trailing edge of this pulse since the input is inverted. On the first slow clock pulse after the "all 1's" condition, all the inputs to gate 66F will be at a logic "0" and thus its output will be at a logic "1". Thus, even though the logic "1" set signal is removed by this time, latch 66G will stay latched in the set condition until the logic "1" signal is removed at its input through gate 60F. Gate 66B has inputs from the output of inverter 66A and from the "Q" outputs of latches 94B, 94C, 94E, 94F and 94G. The "Q" outputs of these five latches will be all a logic "1" when rate counter 94 has counted a number of slow clock pulses corresponding to a 325 msec refractory period. If the output of refractory select output 56 is a logic "0" the output of inverter 66A will be a logic "1". Thus, 325 msec after latch 66G has been set all the inputs to gate 66B will become a logic "1" and its output will also become a logic "1". This output is applied to NOR gate 66F and thus, its output becomes a logic "0". On the trailing edge of the next slow clock pulse latch 66G will be clocked to the condition where its "Q" output is at logic "0" and its "Q̄" output is at a logic "1". The logic "1" signal applied to gate 102D removes the disabling signal from the amp reset circuit discussed above. The signal applied to NOR gate 66F causes its output to remain a logic "0" even after the logic "1" signal from gate 66B is removed, thus latching the refractory circuit into the "off" condition until the next set signal is applied to latch 66G from "all 1's" gate 104A. If the output of refractory select 56 is a logic "1" then the output of inverter 66A is a logic "0" and gate 66B is disabled so that its output does not become a logic "1" at the end of the 325 msec period. In this case, the "Q" output of gate 66D which has inputs from the "Q" outputs of latches 94B, 94E, and 94H will go to a logic "1" at the end of a 400 msec period, and will trigger the termination of the refractory period as discussed above. Gates 66C and 66E have an input from the "Q" output of latch 92C in battery depletion circuit 92. As discussed above, this output is a logic "0" in the normal case when the battery is not depleted. This logic "0" signal disables these gates. However, when the battery becomes depleted the "Q" output of latch 92C goes to a logic "1" enabling these gates. Gate 66C has inputs from the "Q" outputs of latches 94B, 94D, 94F, and 94G. These outputs all become a logic "1" after a period ten percent shorter than the 325 msec period. Thus this gate will produce a logic "1" output prior to the output of gate 66B and terminate the refractory period at an "earlier" time. However, since the slow clock cycle has been extended by the same amount the net result will be that the refractory period stays the same when the battery is depleted. Likewise, gate 66E has connections to the "Q" outputs of latches 94B through 94I such that its output will go to a logic "1" at a ten percent shorter time than the 400 msec period of gate 66D. Thus, if the battery is depleted and the output of refractory select 56 is a logic "1" which disables gate 66C through the input to that gate applied from the output of inverter 66A, then gate 66E will provide an output that will maintain the stable refractory period of 400 msec.

Reversion logic 108 comprises AND gate 108A and latches 108B and 108C. The output of "all 1's" gate 104A is applied to the reset input of latches 108B and 108C. This reset signal ensures that the "Q̄" outputs of latches 108B and 108C are a logic "1" and the "Q" output of latch 108C is at a logic "0" at the beginning of the pulse cycle. As discussed above, the "Q" output of latch 106D has been changed to a logic "0" output by the same "all 1's" signal while the "Q̄" output of latch 66G has been set to a logic "1" by the same signal. The signal from the "Q" output of latch 106D signal is applied to gate 84A so that its output is at a logic "0". The clock input of latch 108D is responsive to the output of inverter 84A in the amp reset circuit, thus each time the amplifier in the analog circuit puts out a signal through amp output 130 latch 108B will be clocked. Since the input to latch 108B is held at a logic "0" no change in its outputs will be caused by such amplifier signals. However, at the end of the 100 msec blanking period the "Q" output of latch 106D becomes a logic "1". Since the other inputs to latch 108B, from the "Q" output of latch 108B and the "Q" output of latch 66G are already a logic "1" the output of gate 108A will change to a logic "1" state. Meanwhile, the logic "1" reset signal has been removed since the output of "all 1's" gate 104A has returned to a logic "0". Thus, the next output of amp output 130 will clock latch 108B so that its "Q" output goes to a logic "0". This signal applied to the input of gate 108A will cause the output of that gate to go to a logic "0" and thus the next signal from amp output 130 will clock the "Q" output of latch 108B back to the logic "1" state. The change in the "Q" output from logic "0" to logic "1" applied to the clock input of latch 108C clocks this latch. Since its data input is at a logic "1" its "Q" output changes to a logic "1" and its "Q̄" output changes to a logic "0". The logic "0" signal is applied to the amp disable gate 102D, to disable the amp reset function as discussed above. Since the data input of latch 108C is held at a logic "1" and the set input is held at a logic "0" the "Q̄" output of latch 108C will remain a logic "0" and the amp reset function will be held disabled until the reversion circuit is reset by another signal from "all 1's" gate 104A. The logic "1" signal is applied to the set input of latch 108B to latch the two reversion latches 108B and 108C in the reversion mode until the next output pulse.

Hysteresis logic 64 comprises inverter 64A, OR gate 64B and latch 64C. The set input of latch 64C is responsive to the "Q" output of latch 84B in the amp reset circuit. As discussed above, if the amp reset circuit is not being held disabled by the refractory, reversion, or reed switch functions, a natural heartbeat detected by the amplifier in analog circuit 14 will produce an output of amp output 130 which causes the "Q" output of latch 84B to go to a logic "1". This signal sets latch 64C causing its "Q" output to go to a logic "1" and its "Q̄" output to go to a logic "0". The latter signal is applied to one of the inputs of each of rate decode gates 60A through 60K, except for gates 60C, the 60-beat-per-minute rate decode gate, and gate 60D, the 50-beat-per-minute rate decode gate. The logic "1" signal is applied as one of the inputs of AND gate 60P in rate decode circuitry 60. If the hysteresis rate output 60Q is at a logic "1" state then the output of gate 60P also becomes a logic "1" which signal is applied through OR gate 60M to gate 60C enabling it. The 60-beat-per-minute gate will then determine the pulse rate as described in the discussion of the output pulse, since its output goes to a logic "1" and resets the rate counter at a rate faster than the 50-beat-per-minute gate. If, however, hysteresis rate output 60Q is a logic "0" then gate 60P will be disabled, its output will be at a logic "0" disabling gate 60M, allowing the 50-beat-per-minute gate to control the output pulse. (Note that the output of gate 60N is a logic "0" since it is also disabled by the logic "0" state of the lower output of latch 64C.) As long as the natural heartbeat remains above the selected hysteresis rate the state of latch 64C will not change, since each heartbeat will set rate counter 94 preventing it from reaching the hysteresis count, and preventing an output pulse from occurring. However, should the heartbeat rate drop below the selected hysteresis rate then the one of gates 60C or 60D which is enabled will have all its inputs go to a logic "1", its output will go to a logic "1" and a pulse will be output from the pulse generator as described above. At the initiation of the output pulse the "Q" output of gate 80B goes to a logic "1" as described above. This signal is applied as one of the inputs to OR gate 64B causing its output to go to a logic "1" which signal is in turn applied to the reset input of latch 64C causing its "Q" output to go to a logic "0" and its "Q̄" output to go to a logic "1". (Note that the set input to latch 64C returned to a logic "0" on the first VCO oscillation after the last detected heartbeat.) The logic "1" state of the "Q" output of latch 64C enables rate gates 60A through 60K and allows the pulse generator to operate at its selected rate. The logic "0" state of the "Q" output of gate 64C disables gate 60P, however if the 60-beat-per-minute rate is selected by the "normal" rate selection outputs 60R through 60U then gate 60N will have a logic "1" output so that the gate 60C is enabled. The pulse generator will continue operating at its selected rate until a detected heartbeat again sets latch 64C. If hysteresis function select output 54 is a logic "0" then the output of inverter 64A is a logic "1" which signal is applied through OR gate 64B to the reset input of latch 64C. This holds the latch reset and enables the pulse generator to continue operating at its selected rate as discussed above. If the output of hysteresis select 54 is a logic "1" then the output of inverter 64A will be a logic "0" and the hysteresis function will operate as discussed.

Threshold margin test logic 122 in FIG. 3a comprises OR gate 122A, latches 122B through 122D, and AND gate 122E. The "Q" output of latch 102A in the amp disable/strobe circuitry 102 is applied as one input of OR gate 122A and to the reset input of latch 122D. As discussed above, this output is at a logic "1" as long as the reed switch 32 is open. The logic "1" signal is applied to the reset inputs of latches 122B and 122C through OR gate 122A, and directly to the reset input of latch 122D. This signal holds the latches in the reset condition. Thus the "Q" outputs of latches 122B and 122C will be in a logic "0" state. These outputs are applied to gate 122E holding its output at a logic "0". This signal is in turn applied to each of gates 62G through 62L in the pulse width decode circuitry holding them disabled. When the Hall effect switch 32 is closed the signal applied to the reset inputs of latches 122B, 122C and 122D changes to a logic "0" at the trailing edge of the first strobe pulse, enabling the gates. The "Q" output of latch 106D in blanking logic 106 is applied to the clock input of latch 122B. When at the end of the first blanking period after the Hall effect switch is closed the "Q" output of latch 106D changes from a logic "0" to a logic "1" latch 122B is clocked. Since its data input is connected to its "Q" output, which was at a logic "1", the clocking changes its "Q" output to logic "1" and its "Q" output changes to a logic "0". The "Q" output of latch 122B is applied to one input of gate 122E and one input of OR gate 60L and the rate decode logic 60. As discussed above in connection with the discussion of the rate decode logic this signal causes the output of gate 60L to go to a logic "1" which selects the 100-pulse-per-minute rate gate. The next output pulse therefore occurs in 600 msec, unless the selected pulse rate is faster than 100-beats-per-minute, in which case a pulse at the selected rate occurs. At the end of the next blanking period latch 122B is again clocked. Its "Q" output changes to a logic "0" and its "Q" output changes to a logic "1". The "Q" output of gate 122B is connected to the clock input of gate 122C, and the "Q" output of gate 122C is connected to its own data input. Since the "Q" output of latch 122C was at a logic "1" state due to the reset signal, the change in the "Q" output of latch 122B clocks the "Q" output of latch 122C to a logic "1" state while its "Q" output goes to a logic "0" state. The "Q" output of latch 122C is applied to one input of gate 122E, but since the other input, which is from the "Q" output of latch 122B, has now gone to a logic "0" the output of gate 122E remains a logic "0". The "Q" output of latch 122C is also applied to gate 60L and causes the next pulse to again be at the 100-beat-per-minute rate. At the end of the next blanking period latch 122B is again clocked, its "Q" output goes to a logic "1" and its "Q" output goes to a logic "0". Gate 122C is not clocked since clocking takes place only on a change in state from logic "0" to logic "1". The logic "1" state of the "Q" output of latch 122B, applied to gate 60L, again causes the next pacemaker pulse to be in 600 msec. However, both inputs to gate 122E are now a logic "1" so that its output is also a logic "1". Thus, the disabling signal is removed from the group "B" gates 62G through 62L in pulse width decode circuitry 62. Each of the gates 62G through 62L are connected to outputs 62M through 62P in the same manner as each of the group "A" gates 62A through 62F respectively. Thus if gate 62A is enabled by pulse width selection circuitry 52 then gate 62G also in enabled, etc. The inputs to gates 62G through 62L respectively are connected to the "Q" outputs of latches 76A through 76H so that each of the gates 62G through 62L will be enabled by a slow clock count that is only seventy five percent of the count that enables the corresponding gate in group "B". Thus, the one of gates 62G through 62L that is enabled by pulse width select circuitry 52 will be enabled by slow clock/PM counter 76 before the corresponding one of the gates in group "A" is enabled. Its output will go to a logic "1" which signal will be applied to OR gate 100A to terminate the output pulse and reset the slow clock/PW counter latches 76A through 76H. Thus the third output pulse after the Hall effect switch is closed will be a pulse having a width seventy five percent of the selected output width. After this output pulse, latch 122B is again clocked by the "Q" output of latch 106D. This causes its "Q" output to go from logic "0" to a logic "1", which clocks latch 122C. The "Q" output of latch 122C in turn goes from logic "0" to logic "1". This signal is applied to the clock input of latch 122D, causing its "Q" output to go to a logic "1" since its data input is held at a logic "1". The "Q" output of latch 122D is applied to the reset inputs of latches 122B and 122C through OR gate 122A. Thus, the logic "1" signal resets latches 122B and 122C. This causes the "Q" outputs of latches 122B and 122C to go to a logic "0", which in turn disables gates 122E and 60L to go to logic "0" allowing the pacemaker to return to its normal operation. The threshold margin test circuitry remains in this state until the Hall effect switch is opened, which continues the reset condition of gates 122B and 122C and also resets gate 122D as discussed above.

|   |
|---|
| X |
| X |
| X |
| X |
| X |
| X |
| X |
| X |
| X |
| X |
| X |

The above description of the invention has been in reference to a particular embodiment. It is evident that those skilled in the art can make numerous uses of, modifications of, and departures from the specific embodiment described herein without departing from the inventive concepts. For example, the Hall effect depends only on the flow of a charge in a magnetic field, thus conductive materials other than silicon may be employed in producing the Hall effect element 210. Various electronic parts of the circuit such as the resistors, transistors, operational amplifiers, and flip-flops may be replaced by equivalent electronic parts. Many other variations may be described. Consequently, the invention is to be construed as embracing each and every novel feature and novel combination of features within the appended claims.

What is claimed is:

1. A body-implantable pulse generator for providing stimulating pulses to living tissue, comprising:
   means for generating said stimulating pulses;
   a semiconductor;
   means for causing an electrical current flow through said semiconductor;
   means for detecting a voltage produced in said semiconductor in a direction perpendicular to the direction of said current flow; and
   means responsive to said means for detecting for controlling said means for generating in response to an externally applied magnetic field.

2. The invention according to claim 1 wherein said semiconductor is composed of silicon.

3. The invention according to claim 1 wherein said means for causing electric current to flow through said semiconductor comprises a means for causing said current to flow for time periods that are shorter than both the time intervals between said periods and the duration of said stimulating pulse.

4. The invention according to claim 3 wherein said means for causing electric current to flow comprises:
   an electrical current source;
   means for generating a timing signal at determined time intervals for said periods of time; and
   means responsive to said signal and communicating with said current source for turning on current to said semiconductor upon the initiation of said signal and turning off current to said semiconductor upon the termination of said signal.

5. The invention according to claim 3 wherein said intervals between said time periods are such that said current is caused to flow at least once each stimulating pulse cycle.

6. The invention according to claim 3 wherein said time periods during which current flows through said semiconductor are less than 200 $\mu$sec.

7. The invention according to claim 1 wherein said means for detecting includes an amplifier responsive to said voltage.

8. The invention according to claim 1 wherein said means for controlling includes a digital circuit and said means for detecting further comprises a means for converting said voltage into a digital signal.

* * * * *

UNITED STATES PATENT AND TRADEMARK OFFICE
CERTIFICATE OF CORRECTION

PATENT NO. : 4,301,804  
DATED : November 24, 1981  
INVENTOR(S) : THOMPSON et al Page 1 of 2

It is certified that error appears in the above-identified patent and that said Letters Patent are hereby corrected as shown below:

Column 15,  
    Line 28, "105" should be --106--;

Column 17,  
    Line 40, "lable" should be --label--;

Column 18,  
    Line 32, ""$\overline{Q}$"" should be --"Q"--;

Column 18,  
    Line 32, "fliop-flops" should be --flip-flops--;

Column 18,  
    Line 54, "becmes" should be --becomes--;

Column 19,  
    Line 30, ""$\overline{Q}$"" should be --"Q"--;

Column 19,  
    Line 40, ""Q"", should be --"$\overline{Q}$"--;

Column 20,  
    Line 65, "gats" should be --gates--;

Column 21,  
    Line 10, "ANd" should be --AND--;

Line 26, remove "to";

Line 35, "bottom" should be --<u>bottom</u>--

Line 57, after "output" (second occurrence) insert --110--;

UNITED STATES PATENT AND TRADEMARK OFFICE
CERTIFICATE OF CORRECTION

PATENT NO. : 4,301,804

DATED : November 24, 1981

INVENTOR(S) : THOMPSON et al

It is certified that error appears in the above-identified patent and that said Letters Patent are hereby corrected as shown below:

Column 23,
    Line 4, "54" should be --52--;

Column 24,
    Line 33, "output" should be --input--;

Column 26,
    Line 47, "of" should be --to--;

Column 27,
    Line 4, ""Q"", should be --$\overline{"Q"}$--;

Line 63, ""Q"", should be --$\overline{"Q"}$--;

Column 30,
    Line 28, "clock/PM" should be --clock/PW--.

Signed and Sealed this

Eighth Day of June 1982

|SEAL|

Attest:

GERALD J. MOSSINGHOFF

Attesting Officer     Commissioner of Patents and Trademarks